(12) United States Patent
Snoke

(10) Patent No.: US 6,464,682 B1
(45) Date of Patent: *Oct. 15, 2002

(54) METHOD OF EPIDURAL SURGERY

(75) Inventor: Phillip Jack Snoke, Atlanta, GA (US)

(73) Assignee: Catheter Imaging Systems, Inc., Suwanee, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/476,847

(22) Filed: Jan. 3, 2000

Related U.S. Application Data

(63) Continuation of application No. 09/066,884, filed on Apr. 27, 1998, now Pat. No. 6,010,493, which is a continuation of application No. 08/957,998, filed on Oct. 22, 1997, now Pat. No. 5,857,996, which is a continuation of application No. 08/606,084, filed on Feb. 23, 1996, now abandoned, which is a continuation of application No. 08/321,174, filed on Oct. 11, 1994, now Pat. No. 5,496,269, which is a continuation of application No. 08/129,331, filed on Sep. 30, 1993, now Pat. No. 5,354,266, which is a continuation-in-part of application No. 07/908,403, filed on Jul. 6, 1992, now Pat. No. 5,342,299, which is a continuation-in-part of application No. 07/963,431, filed on Oct. 19, 1992, now Pat. No. 5,423,311, which is a continuation-in-part of application No. 07/970,490, filed on Nov. 2, 1992, now Pat. No. 5,399,164.

(51) Int. Cl.$^7$ .............................................. A61M 31/00
(52) U.S. Cl. ................... 604/510; 604/508; 604/95.01; 604/95.04
(58) Field of Search ........................... 604/28, 48, 500, 604/506, 508, 510, 95.01–95.05; 128/898; 600/433

(56) References Cited

U.S. PATENT DOCUMENTS

| | | |
|---|---|---|
| 922,985 A | 10/1909 | Wappler |
| D202,552 S | 10/1965 | Rose .................... D24/137 |
| 3,470,876 A | 10/1969 | Barchiton .................... 128/348 |
| 3,500,820 A | 3/1970 | Almen ........................ 604/95 |
| 3,605,725 A | 9/1971 | Bentov |

(List continued on next page.)

FOREIGN PATENT DOCUMENTS

| | | |
|---|---|---|
| DE | 1213571 | 3/1966 |
| DE | 3916288 A1 | 11/1989 |
| DE | 0489937 A1 | 7/1990 |
| EP | 0 343 094 | 1/1989 |
| EP | 0 370 158 | 5/1990 |

(List continued on next page.)

OTHER PUBLICATIONS

US 4,986,258, 1/1991, Cho et al. (withdrawn)
Declaration of Dr. Dennis W. Coombs dated Nov. 19, 1996 in Myelotec, Inc. and Edward J. Lortie, Jr., v. Catheter Imaging Systems, Inc. pp. 1–4.
Declaration of Dr. Yasin Kahn in Myelotec, Inc. and Edward J. Lortie, Jr., v. Catheter Imaging Systems, Inc., pp. 1–2.Myelotec, Inc. and Edward J. Lortie, Jr., v. Catheter Imaging Systems, Inc.

(List continued on next page.)

Primary Examiner—Brian L. Casler
Assistant Examiner—Cris L. Rodriguez
(74) Attorney, Agent, or Firm—Bracewell & Patterson, L.L.P.

(57) ABSTRACT

A method of epidural surgery is provided that improves visibility in the epidural space of a patient for more effectively conducting therapeutic surgery therein. The method includes the steps of distending a portion of the epidural space of a patient by filling the portion of the epidural space with a fluid supplied from a catheter and positioning a portion of an optical scope in the distended portion of the epidural space by inserting the optical scope through the same catheter that supplies the distending fluid to thereby provide a visual image of the epidural space.

19 Claims, 8 Drawing Sheets

U.S. PATENT DOCUMENTS

| | | | |
|---|---|---|---|
| 3,625,200 A | 12/1971 | Muller | 128/2.05 |
| 3,773,034 A | 11/1973 | Burns et al. | 604/95 |
| 3,788,304 A | 1/1974 | Takahashi | 128/6 |
| 3,831,017 A | 8/1974 | Auer | 240/2 |
| 3,892,228 A | 7/1975 | Mitsui | 128/4 |
| 3,948,251 A | 4/1976 | Hosono | 128/4 |
| D243,115 S | 1/1977 | Ziegler et al. | D24/138 |
| 4,273,111 A | 6/1981 | Tsukaya | 128/6 |
| 4,279,245 A | 7/1981 | Takagi et al. | 128/4 |
| 4,327,723 A | 5/1982 | Frankhouser | 128/214.4 |
| 4,344,092 A | 8/1982 | Miller | 358/217 |
| 4,353,358 A | 10/1982 | Emerson | 128/4 |
| 4,390,012 A | 6/1983 | Mizumoto | 128/4 |
| 4,413,278 A | 11/1983 | Feinbloom | 358/93 |
| 4,417,886 A | 11/1983 | Frankhouser et al. | 604/53 |
| 4,421,106 A | 12/1983 | Uehara | 128/4 |
| 4,433,675 A | 2/1984 | Konoshima | 128/6 |
| 4,475,539 A | 10/1984 | Konomura | 128/6 |
| 4,483,326 A | 11/1984 | Yamaka et al. | 128/4 |
| 4,515,592 A | 5/1985 | Frankhouser | 604/163 |
| 4,535,773 A * | 8/1985 | Yoon | |
| 4,539,586 A | 9/1985 | Danna et al. | 358/98 |
| 4,543,090 A | 9/1985 | McCoy | 604/95 |
| 4,545,374 A | 10/1985 | Jacobson | 128/303 |
| 4,551,292 A | 11/1985 | Fletcher et al. | 264/139 |
| 4,563,181 A | 1/1986 | Wijayarathna et al. | 604/280 |
| 4,573,448 A | 3/1986 | Kambin | 128/1 R |
| 4,577,621 A | 3/1986 | Patel | 128/4 |
| 4,580,551 A | 4/1986 | Siegmund et al. | 128/4 |
| 4,587,972 A | 5/1986 | Morantte, Jr. | 128/660 |
| 4,589,404 A | 5/1986 | Barath et al. | 128/6 |
| 4,590,923 A | 5/1986 | Watanabe | 128/6 |
| 4,601,284 A | 7/1986 | Arakawa et al. | 128/6 |
| 4,611,888 A | 9/1986 | Prenovitz et al. | 350/96.22 |
| D286,280 S | 10/1986 | Holtman et al. | D24/107 |
| 4,625,713 A | 12/1986 | Hiraoka | 128/4 |
| 4,644,960 A | 2/1987 | Johans | 128/786 |
| 4,649,904 A | 3/1987 | Krauter et al. | 128/6 |
| 4,651,202 A | 3/1987 | Arakawa | 358/98 |
| 4,653,476 A | 3/1987 | Bonnet | 128/4 |
| 4,713,057 A | 12/1987 | Huttner et al. | 604/164 |
| 4,737,142 A | 4/1988 | Heckele | 604/95 |
| 4,745,908 A | 5/1988 | Wardie | 128/6 |
| 4,748,969 A | 6/1988 | Wardle | 128/4 |
| 4,750,475 A | 6/1988 | Yoshihashi | 128/6 |
| 4,753,222 A | 6/1988 | Morishita | 128/4 |
| 4,758,222 A | 7/1988 | McCoy | 604/95 |
| 4,776,844 A | 10/1988 | Ueda | 604/95 |
| 4,782,819 A | 11/1988 | Adair | 604/280 |
| 4,791,912 A | 12/1988 | Tashiro | 128/4 |
| 4,793,326 A | 12/1988 | Shishido | 128/4 |
| 4,797,737 A | 1/1989 | Yazawa | 358/98 |
| 4,799,496 A | 1/1989 | Hargreaves et al. | 128/772 |
| 4,808,157 A | 2/1989 | Coombs | 604/44 |
| 4,815,450 A | 3/1989 | Patel | 128/6 |
| 4,834,710 A | 5/1989 | Fleck | 604/171 |
| 4,844,053 A | 7/1989 | Dittrich | 128/4 |
| 4,853,773 A | 8/1989 | Hibino et al. | 358/98 |
| 4,867,529 A | 9/1989 | Utsumi et al. | 350/96.25 |
| 4,884,133 A | 11/1989 | Kanno et al. | 358/98 |
| 4,888,146 A | 12/1989 | Dandeneau | 264/171 |
| 4,890,602 A | 1/1990 | Hake | 128/4 |
| 4,893,613 A | 1/1990 | Hake | 128/4 |
| 4,901,142 A | 2/1990 | Ikuno et al. | 358/98 |
| 4,904,237 A | 2/1990 | Janese | 604/28 |
| 4,905,666 A | 3/1990 | Fukuda | 128/4 |
| 4,906,230 A | 3/1990 | Maloney et al. | 604/95 |
| 4,911,148 A | 3/1990 | Sosnowski et al. | 128/6 |
| 4,919,112 A | 4/1990 | Siegmund | 128/4 |
| 4,919,653 A | 4/1990 | Martinez et al. | 604/117 |
| 4,920,413 A | 4/1990 | Nakamura et al. | 358/98 |
| 4,924,856 A | 5/1990 | Noguchi | 128/6 |
| 4,930,521 A | 6/1990 | Metzger et al. | 128/786 |
| 4,933,816 A | 6/1990 | Hug et al. | 362/32 |
| 4,934,340 A | 6/1990 | Ebling et al. | 128/6 |
| 4,941,455 A | 7/1990 | Watanabe et al. | 128/4 |
| D310,721 S | 9/1990 | Beisang, III | D24/128 |
| 4,954,129 A | 9/1990 | Giuliani et al. | 604/53 |
| 4,968,295 A | 11/1990 | Neumann | 604/6 |
| 4,968,298 A | 11/1990 | Michelson | 604/36 |
| 4,972,828 A | 11/1990 | Ito | 128/4 |
| 4,973,312 A | 11/1990 | Andrew | 604/158 |
| 4,973,329 A | 11/1990 | Park et al. | 606/1 |
| 4,979,496 A | 12/1990 | Komi | 128/4 |
| 4,983,165 A | 1/1991 | Loiterman | 604/95 |
| 4,983,585 A * | 1/1991 | Pennell et al. | |
| 4,985,022 A | 1/1991 | Fearnot et al. | 604/282 |
| 4,989,582 A | 2/1991 | Sakiyama et al. | 128/6 |
| 4,996,974 A | 3/1991 | Ciarlei | 128/4 |
| 5,004,456 A | 4/1991 | Botterbusch et al. | 604/53 |
| 5,010,875 A | 4/1991 | Kato | 128/6 |
| 5,024,655 A | 6/1991 | Freeman et al. | 604/53 |
| 5,042,915 A | 8/1991 | Akutsu et al. | 359/230 |
| 5,053,046 A | 10/1991 | Janese | 606/215 |
| 5,058,568 A | 10/1991 | Irion et al. | 128/4 |
| 4,539,586 A | 12/1991 | Danna et al. | |
| 5,078,702 A | 1/1992 | Pomeranz | 604/280 |
| 5,084,043 A | 1/1992 | Hertzman et al. | 606/3 |
| 5,085,631 A | 2/1992 | Leighton | 604/28 |
| 5,090,959 A | 2/1992 | Samson et al. | 604/96 |
| RE33,854 E | 3/1992 | Adair | 128/6 |
| 5,101,807 A | 4/1992 | Kawashima | 128/6 |
| 5,114,414 A * | 5/1992 | Buchbinder | |
| 5,125,906 A | 6/1992 | Fleck | 604/171 |
| 5,127,393 A | 7/1992 | McFarlin et al. | 128/4 |
| 5,131,382 A | 7/1992 | Meyer | 128/6 |
| 5,134,469 A | 7/1992 | Uchimura | 358/98 |
| 5,143,475 A | 9/1992 | Chikama | 403/291 |
| 5,151,096 A | 9/1992 | Khoury | 606/15 C |
| 5,160,559 A | 11/1992 | Scovil et al. | 156/73.6 |
| 5,167,221 A | 12/1992 | Chikama | 128/4 |
| 5,168,864 A | 12/1992 | Shockey | 128/4 |
| 5,188,594 A | 2/1993 | Zilberstein | 604/51 |
| 5,195,541 A | 3/1993 | Obenchain | 128/898 |
| 5,197,649 A | 3/1993 | Bessler et al. | 227/179 |
| 5,199,417 A | 4/1993 | Muller et al. | 128/6 |
| 5,199,950 A | 4/1993 | Schmitt et al. | 604/95 |
| 5,215,105 A | 6/1993 | Kizelshteyn et al. | 128/898 |
| 5,217,454 A | 6/1993 | Khoury | 606/7 |
| D338,958 S | 8/1993 | Jensen | D24/133 |
| 5,232,442 A | 8/1993 | Johnson et al. | 604/51 |
| 5,251,611 A * | 10/1993 | Zehel et al. | |
| 5,267,573 A | 12/1993 | Evans et al. | 604/95 |
| 5,273,535 A | 12/1993 | Edwards et al. | 604/95 |
| D343,678 S | 1/1994 | Snoke et al. | 604/95 |
| 5,275,151 A * | 1/1994 | Shockey et al. | |
| 5,282,472 A * | 2/1994 | Companion et al. | |
| D347,473 S | 5/1994 | Nitzsche | |
| 5,325,845 A * | 7/1994 | Adair | |
| 5,328,467 A | 7/1994 | Edwards et al. | |
| D349,340 S | 8/1994 | Snoke et al. | D24/138 |
| 5,342,299 A | 8/1994 | Snoke et al. | 604/95 |
| D350,605 S | 9/1994 | Williams | D24/133 |
| 5,344,397 A | 9/1994 | Heaven et al. | 604/95 |
| D351,652 S | 10/1994 | Thompson et al. | D24/112 X |
| 5,354,266 A | 10/1994 | Snoke | 604/28 |
| 5,377,668 A * | 1/1995 | Ehmsen et al. | |
| 5,396,880 A | 3/1995 | Kagan et al. | 128/6 |
| 5,399,164 A | 3/1995 | Snoke et al. | 604/95 |
| 5,415,158 A | 5/1995 | Barthel et al. | 604/95 |
| D359,801 S | 6/1995 | Buyhin et al. | D24/112 |

| | | | |
|---|---|---|---|
| 5,423,311 A | 6/1995 | Snoke et al. ................... | 128/6 |
| 5,437,636 A | 8/1995 | Snoke et al. ................... | 128/95 |
| 5,496,269 A | 3/1996 | Snoke ........................... | 604/28 |
| 5,526,820 A | 6/1996 | Khoury ....................... | 128/748 |
| 5,531,687 A | 7/1996 | Snoke et al. ................... | 604/95 |
| 5,542,924 A | 8/1996 | Snoke et al. ................... | 604/95 |
| D382,959 S | 8/1997 | Arpe ........................... | D24/112 |
| D384,746 S | 10/1997 | Musgrave et al. ......... | D24/112 |
| 5,830,209 A * | 11/1998 | Savage et al. | |
| 5,857,996 A | 1/1999 | Snoke ........................... | 604/28 |
| 6,010,493 A | 1/2000 | Snoke ........................... | 604/510 |

FOREIGN PATENT DOCUMENTS

| | | |
|---|---|---|
| EP | 0389453 | 9/1990 |
| EP | 0 489 937 | 6/1992 |
| FR | 990417 | 9/1951 |
| FR | 2 655 548 | 6/1991 |
| WO | WO88/00810 | 2/1988 |
| WO | WO91 01772 | 2/1991 |
| WO | WO91/11213 | 8/1991 |
| WO | WO93/15648 | 8/1993 |
| WO | WO94/27666 | 12/1994 |

OTHER PUBLICATIONS

Declaration of Dr. Luke M. Kitahata dated 11–1 Myelotec, Inc. and Edward J. Lortie, Jr., v. Catheter Imaging Systems, Inc., pp. 1–3.

Declaration of Ronald G. Seifert dated Nov. 18, 1996 in Myelotec, Inc. and Edward J. Lortie, Jr., v. Catheter Imaging Systems, Inc., pp. 1–2.

Affidavit of Thomas R. Long executed Nov. 11, 1996 in Myelotec, Inc. and Edward J. Lortie, Jr., v. Catheter Imaging Systems, Inc., pp. 1–17.

Deposition of Jack Snoke , dated Oct. 24, 1996, in Myelotec, Inc. and Edward J. Lortie, Jr., v. Catheter Imaging Systems, Inc., pp. 1–11.

Affidavit of Randy Frank Rizor, M.D., executed 9–20–956 in Myelotec, Inc. and Edward J. Lortie, Jr., v. Catheter Imaging Systems, Inc., pp. 1–5.

Affidavit of Geoffrey Harrison Galley executed Sep. 7, 1994 pp. 1–7.

Affidavit of Vernon Milton Levey executed Sep. 7, 1994 pp. 1–2.

Affidavit of Paul Z. Lundbergh dated Nov. 12, 1996 in Myelotec, Inc. and Edward J. Lortie, Jr., v. Catheter Imaging Systems, Inc., (3 pages and attached Exhibits A and B).

Affidavit of Hurley J. Blakeney dated Oct. 6, 1996, in Myelotec, Inc. and Edward J. Lortie, Jr., v. Catheter Imaging Systems, Inc., pp. 1–7.

Lortie, Jr., v. Catheter Imaging Systems, Inc., pp. 1–3.

Affidavit of David Clatworthy executed Nov. 6, 1996 in Myelotec, Inc. and Edward J. Lortie, Jr., v. Catheter Imaging Systems, Inc., pp. 1–7.

Angio Las Ultra–Vu™ brochure, pp. 1–3.

Deposition of Adib Issaac Khoury dated Oct. 10, 1996 Condensed Transcript and Concordance in Myelotec, Inc. and Edward J. Lortie, Jr., v. Catheter Imaging Systems, Inc., pp. 1–17.

Deposition of P. Jack Snoke Oct. 24, 1996 in Myelotec, Inc. and Edward J. Lortie, Jr., v. Catheter Imaging Systems, Inc.,, pp. 1–99.

Exhibits 1–13 to Deposition of P. Jack Snoke Oct. 24, 1996 in Myelotec, Inc. and Edward J. Lortie, Jr., v. Catheter Imaging Systems, Inc., pp. 1–68.

Videotape Deposition of Lloyd Saberski, M.D., Nov. 7, 1996, in Myelotec, Inc. and Edward J. Lortie, Jr., v. Catheter Imaging Systems, Inc., pp. 1–118.

Deposition of Ron Luther, Nov. 6, 1996, Condensed Transcript and Concordance in Myelotec, Inc. and Edward J. Lortie, Jr., v. Catheter Imaging Systems, Inc., pp. 1–19.

Cirriculum Vitae of Neil Kahanovitz, M.D. pp. 1–31.

Deposition of Neil Kahanovitz, M.D. Nov. 15, 1996, Condensed Transcript and Concordance in Myelotec, Inc. and Edward J. Lortie, Jr., v. Catheter Imaging Systems, Inc., pp. 1–9.

Deposition of Dan Page, Nov. 15, 1996. Condensed Transcript and Concordance in Myelotec, Inc. and Edward J. Lortie, Jr., v. Catheter Imaging Systems, Inc., pp. 1–7.

Deposition of Edward J. Lortie, Jun. 30, 1994 in Catheter Imaging Systems, Inc., v. Edward J. Lortie, Jr., Civil Action E23514, pp. 1–129.

Deposition of Edward J. Lortie, Jun. 30, 1994 in Myelotec, Inc. and Edward J. Lorite, Jr., v. Catheter Imaging Systems, Inc., pp. 1–153.

"Dynspace Systems, Inc. Introduces The New Epidural Ultra VU* Scope System" from ASA Mee4ting San Francisco, CA Oct. 28–31, 1991 pp. 1–4.

"Epidual Endoscopy Excerpts and Comments" Yale University School of Medicine Center for Pain Management; Apr. 1992.

"Exploring Epidural Endoscopy" The Ultra–Vu™ Scope in Pain Management Applicati "Experimental Procedures at Yale University by Dr. Randy Rizor," Apr. 6, 1992—Tape 1 of 3 ons; Apr. 1992.

"Experimental Procedures at Yale University by Dr. Randy Rizor," Apr. 6, 1992—Tape 1 of 3.

"Experimental Procedures at Yale University by Dr. Randy Rizor," Apr. 6, 1992—Tape 2 of 3.

"Experimental Procedures at Yale University by Dr. Randy Rizor," Apr. 6, 1992—Tape 3 of 3.

Second Affidavit of Randy Frank Rizor, M.D. dated Nov. 13, 1996.

AngioLaz Ultra–Vu™, Angiolaz Epidural Ultra–Vu Scope.

*Anesthesiology* Pain Managment in the $21^{st}$ Century: An Anesthesiologist's Look into the Crystal Ball, Steven D. Waldman, M.D.

Eighteen–Gauge Microscopic–Telescopic Needle Endoscope with Electrode Channel: Potential Clinical and Research Application, Charles P. Olinger, M.D. and R. L. Ohlhaber, *Surg. Neuol.* vol. 2, May 1974.

"The Dorsomedian Connective Tissue Band in the Lumbar Epidural Space of Humans: An Anatomical Study Using Epiduroscopy in Autopsy Cases" Rune Blomberg, M.D. 1986 by the International Anesthesia Research Society.

Physiology, Pathophysiology and Pharmacology of Local Anaesthetics Used in Regions1 Anaesthesia, presented by B. G. Covino and G. T. Tucker.

Hogan, Quinn H., M.D., "Lumbar Epidural Anatomy", *Anesthesiology*, vol. 75, pp. 767–775 (1991).

Pick et al., "Endoscopic Examinations and Computed Tomography Concerning Cervical Spine Positioning in Treatment of Acute Cervical Spine Injuries", *Archives of Orthopaedic and Traumatic Surgery*, vol. 97, pp. 43–49 (1980).

Pool, Lawrence J., "Direct Visualization of Dorsal Nerve Roots of the Cauda Equina by Means of Myeloscope", *Archives of Neurology and Psychiatry*, pp. 1308–1312.

Harrison et al., "Resin Injection Studies of the Lumbar Extradural Space", *British Journal of Anaesthesia*, vol. 57, pp. 333–336 (1985).

Blomberg, R., "A Method for Epiduroscopy and Spinaloscopy", *Acta Anaesthesiology Scand*, vol. 29, pp. 113–116 (1985).

Ooi et al., "Myeloscopy, with Special Reference to Blood Flow Changes in the Cauda Equina During Lasègue's Test", *Int'l Orthopaedics (SICOT)*, vol. 4, pp. 307–311 (1981).

Shimoji et al., "Observation of Spinal Canal and Cisternae with the Newly Developed Small-diameter, Flexible Fiberscopes", *Anesthesiology*, vol. 75, pp. 341–344 (1991).

Blomberg et al., "The Lumbar Epidural Space in Patients Examined with Epiduroscopy", *Aneth Analg*, vol. 68, pp. 157–160 (1989).

Stern, Lincoln E., "The Spinascope: A New Instrument for Visualizing the Spinal Canal and Its Contents", *Medical Record*, pp. 31–32 (1936).

Ooi et al., "Myeloscopy", *Int'l Orthopaedics (SICOT)*, vol. 1, pp. 107–111 (1977).

Burman, Michael S., "The Direct Visualization of the Spinal Canal and Its Contents", pp. 695–696.

Pool, Lawrence J., "Myeloscopy: Intraspinal Endoscop," *Surgery*, vol. 11, pp. 169–182 (2/42).

Waldman, Steven D., "Pain Management in the 21st Century: An Anesthesiologist's Look Into the Crystal Ball," *American Journal of Pain Management*, vol. 1 (10/91).

Hillmer, Michael, "Back Talk," *Spirit*, p. 32 (10/91).

Springer, Ilene, "Back Talk," p. 114, 118, 122.

Shantha 3et al., "Subdural Blood Patch for Spinal Headache," *The New England Journal of Medicine*, vol 325, No. 17, pp. 1252–1253 (10/91).

*Caudal Analgesia*, pp. 264–265.

"Actual Position of Spinal and Epidural Anaesthesia," pp. 42–43.

"Insertion of the Catheter," *Continuous Epidual Analgesia*, pp. 218–223.

"Sacral Epidual (Caudal) Block," *Principles and Practice of Regional Anaesthesia*, pp. 105–106, 108.

"Spinal Analgesia," *Anatomy*, p. 61.

Fortuna, Armando, "Caudal Epidual Anesthesia in Latin–America," p. 928.

Bromage, *Drugs and Equipment*, pp. 333–334.

Hogan et al., "Epidual Steroids and the Outcomes Movement," Pain Digest, vol. 1, pp. 269–270 (1992).

"Epidural Endoscopy Excerpts and Comments" Yale University School of Medicine, Center for Pain Management:; Apr. 1992.

"Exploring Epidural Endoscopy" Diagnostic Images Using the Ultra–Vu™ Scopy in Pain Management Applications; Apr. 1992.

Exploring Epidural Endoscopy Diagnostic Imnages Using the Ultra–Vu™ Scopy; Apr. 1992.

"Experimental Procedures at Yale University by Dr. Randy Rizor," Apr. 16, 1992—Tape 1 of 3.

Experimental Procedures at Yale University by Dr. Randy Rizor, Apr. 6, 1992—Tape 2 of 3.

"Experimental Procedures at Yale University by Dr. Randy Rizor," Apr. 16, 1992—Tape 3 of 3.

"Notice of Arbitration Award" Pursuant to 37 CFR 1.335 and 35 U.S.C.§ 294 In re U. S. Patent of: Phillip Jack Snoke Serial No. 08/321,174—Patent No. 5,496,269 for Method of Epidural Surgery.

"Notice of Arbitration Award" Pursuant to 37 CFR 1.335 and 35 U.S.C. §294 in re U. S. Patent Of: Phillip Jack Snoke Serial No. 08/129,331—Patent No. 5,354,266 for Method of Epidural Surgery.

Seldinger, Sven I., "Catheter Replacement of the Needle in Percutaneous Arteriography," *American Journal of Roentgenology*, vol. 142, pp. 5–7 (1984).

Catheter Imaging Systmes, Inc. v. Meylotec, Inc. and Edward J. Lortie, Jr., Civil Action 1–97–CV–0025 *Notice of Petitioner's Motion to Confirm Arbitration Award* filed in U. S. Patents 5,354,266 and 5,496,269 (28 pages).

Arbitrator's Order Re: Construction of Claims In The Matter Of: Electro–Biology, Inc. V. Visionary Biomedical, Inc. Civil Action No. 1:99–CV–2801–RWS(STAYED)Jan. 17, 2001.

Arbitrator's Memorandum and Final Order In The Matter Of: Electro–Biology, Inc., v. Visionary Biomedical, Inc. Civil Action No. 1:99–CV–2801–RWS (STAYED).

Office Action Dated Aug. 1, 1994; U.S. Ser. No. 07/970,490; Filing Date Nov. 2, 1992; Exhibit No. 2A.

Examiner Interview Summary Record Dated Nov. 8, 1994; U.S. Ser. No. 07/970,490; Filing Date Nov. 2, 1992; Exhibit No. 2B.

Amendment in response to Office Action mailed Aug. 1, 1994 and the interview of Nov. 8, 1994; U.S. Ser. No. 07/970,490; Filing Date Nov. 2, 1992; Exhibit 2C.

Preliminary Amendment; Dec. 30, 1994; U.S. Ser. No. 08/279,500; Filing Date Jul. 22, 1994; Exhibit 4A.

Office Action Dated Sep. 25, 1995; U.S. Ser. No. 08/367,105; Filing Date Jul. 22, 1994; Exhibit No. 4B.

Examiner Interview Summary Record dated Nov. 14, 1995; Exhibit No. 4C.

Amendment responsive to Official Action mailed Sep. 25, 1995; U.S. Ser. No. 08/367,105; Filing Date Jul. 22, 1994; Exhibit No. 4D.

Preliminary Amendment;Jan. 13, 1995; U.S. Ser. No. 07/970,490; Filing Date Nov. 2, 1992; Exhibit No. 5A.

Office Action Dated Jan. 26, 1998; U.S. Ser. No. 08/957,998; Filing Date Oct. 22, 1997;Exhibit No. 6A.

Interview Summary Dated May 12, 1998; U.S. Ser. No. 08/957,998; Filing Date Oct. 22, 1997; Exhibit No. 6B.

Notice of Allowability Dated Aug. 6, 1998; U.S. Ser. No. 08/957,998; Filing Date Oct. 22, 1997; Exhibit No. 6C.

Office Action Dated Apr. 15, 1997; U.S. Ser. No. 08/606,084; Filing Date Exhibit No. 6D.

Supplemental Citation Under 37 CFR §1.97; Aug. 27, 1998; U.S. Ser. No. 09/066,884; Filing Date Apr. 27, 1998; Exhibit No. 7A.

Office Action Dated Oct. 22, 1998; U.S. Ser. No. 09/066,884; Filing Date Apr. 27, 1998; Exhibit No. 7B.

Signed May 1995 Settlement Agreement between; Catheter Imaging Systems, Inc., P. Jack Snoke, Michael J. Mark, William J. Mack, Myelotec, Inc., Edward Lortie; Exhibit No. 8.

James Grant @ Alston & Bird Nov. 21, 1995 Cease & Desist letter to Edward Lortie and William Johnson; Exhibit No. 10.

Aug. 12, 1997 Jack Snoke letter to John Moore, Vice President, Electro–Biology, Inc.; Exhibit No. 11.

Sample of Sun Catheter; Exhibit No. 13.

James Pastena Apr. 20, 1999 letter to Edward Lortie; Exhibit No. 14.

Videotape—Exploring Epidural Endoscopy Maddison Avenue, AngioLaz Ultra VU Scope @ with attached transcript; Exhibit No. 15.
EBI Vue Cath Packaging Back Label; Exhibit No. 16A, EBI Vur Cath Catheter; Exhibit No. 16B, EBI Vue Cath Catheter Plastic Packaging Tray; Exhibit No. 16C.
Label for EBI Vue Cath; Exhibit 17A.
Tray for EBI VUE Cath; Exhibit 17B.
Updated drawing of Catheter entitled Uni–Directional Steerable Catheter Assembly. Updated Drawing of Pistol Grip Catheter Device entitled Uni–Directional Steerable Catheter Assembly; Exhibit No. 19.
James Pastena Dec. 18, 1996 letter to Jack Snoke and Michael Mark; Exhibit No. 21.
Jack Snoke Sep. 16, 1997 letter to Martin Wynkoop; Exhibit No. 22.
Jack Snoke Aug. 25, 1997 Memo to Dan Page; Exhibit No. 23.
Pacesetter Systems, Inc., Back Scope System Development, Mar. 23, 1992; Exhibit No. 24.
Videotape—Discussions with Dr. Saberski Apr. 6, 1992; Exhibit No. 25.
Videotape—Epidural Endoscopy, Exercise and Comments, Yale University School of Medicine Center for Pain Managment; Exhibit No. 26.
Dick Dickerson Dec. 5, 1997 letter to Russell Rizor and unsigned Rizor Consulting Agreement; Exhibit No. 27.
Michael Mark Sep. 28, 1992 letter to Randy Rizor; Exhibit No. 28.
Myeloscopy Review by Dr. Randy Rizor; Exhibit No. 29.
Physician Pain Specialists, Outline of Equipment and Procedure for Nursing Reviewal; Exhibit No. 30.
Draft of case reports sent to Dr. Saberski; Exhibit No. 31.
Affidavit of Randy Frank Rizor executed Sep. 20, 1996 in Myelotec, Inc., and Edward J. Lortie, Jr., v. Catheter Imaging Systems, Inc.; Exhibit No. 32.
Second Affidavit of Randy Frank Rizor executed Nov. 13, 1996 in Myelotec, Inc., and Edward J. Lortie, Jr., v. Catheter Imaging Systems, Inc.; Exhibit No. 33.
Sworn Statement of Randy Frank Rizor Sep. 11, 1996 in Myelotec, Inc., and Edward J. Lortie v. Catheter Imaging Systems; Exhibit No. 34.
Randy Rizor Jun. 8, 1992 letter to Dr. David Brandenburg of St. Joseph's Hospital, Atlanta, GA.
Videotape—Raw Footage of Yale, Angio Laz Tapes S1,S2, S3; Exhibit No. 36.
Videotape—Raw Footage of Yale, Angio Laz Tapes S4, S5, S6; Exhibit No. 37.
Videotape—Raw Footage of Yale, Angio Laz Tapes S7, S8, S9; Exhibit No. 38.
Randy Rizor Apr. 14, 1992 letter to Lloyd Saberski; Exhibit No. 39.
Randy Rizor Aug. 12, 1992 letter to Ed Lorti; Exhibit No. 40.
Mar. 28, 1996 FDA Meeting Documents; Exhibit No. 41.
Marty Wynkoop Memo to VueCath Endoscopic System Team re: Surgery with Dr. Rizor and Associates; Exhibit No. 42.
Randy Rizor Apr. 4, 1997 letter to Martin Wynkoop; Exhibit No. 43.
Marty Wynkoop Apr. 7, 1997 Memo to Rich Dickerson re; Dr. Rizor visit on Apr. 3, 1997 & Apr. 4, 1997;Discussing clear tip; Exhibit No. 44.

Jack Snoke Aug. 28, 1997 letter to John S. Moore, Vice President of Development, Electro–Biology, Inc.; Exhibit No. 45.
Randy Rizor Feb. 4, 1998 letter to Martin Wynkoop; Exhibit No. 46.
Martin Wynkoop Aug. 27, 1999 letter to Randy Rizor; Exhibit No. 47.
Myeloscopy Workshop Syllabus, Randy F. Rizor, M.D., ASRA Comprehensive Review of Pain Management, Nov. 19, 1999; Exhibit No. 48.
AngioLaz Drawing; Exhibit No. 49.
Notice of Deposition and Subpoena of Jeffrey S. Whittle in Electro–Biology, Inc., v. Visionary Biomedical, Inc., Edward J. Lortie and Adib I. Khoury; Exhbit No. 50.
Declaration in Support of Petition for Correction of Inventorship in Application 07/970,490 ('164 Patent); Exhibit No. 51.
Patent 5,857,996, pp. 1–4; Exhibit No. 52.
Affidavit of John Snowdon in Myelotec, Inc., and Edward J. Lortie, Jr., v. Catheter Imaging Systems, Inc.; Exhibit No. 53.
Supplemental Citation of Prior Art in Application 08/957, 998 ('996 Patent); Exhibit No. 54.
Response to Final Office Action in pending application 09/351,388 Exhibit No. 60.
Mar. 7, 1995 EBI/CIS Financial Analysis; Exhibit No. 61.
Mar. 7, 1995 EBI/CIS Financial Analysis; Exhibit No. 62.
1995 Medical Data International, Inc., Orthopedic Endoscopic Procedures, Market Forecast, 1992,1995,1998 and 2000; Procedures Eligible for the Use of Viewing Systems, 1992, 1995,1998 and 2000; Exhibit No. 63.
EBI Response to Myelotec Interrogatories in Electro–Biology, Inc. v. Myelotec, Inc.,Edward J. Lortie, and Adib I. Khoury; Exhibit No. 64.
EBI Supplemental Response to Myelotec Interrogatories in Electro–Biology, Inc, v. Myelotec, Inc., Edward J. Lortie, and Adib I. Khoury; Exhibit No. 64A.
Jack Snoke Dec. 31, 1996 letter to James Pastena; Exhibit No. 65.
Michael Mark Aug. 26, 1997 to James Pastena re: Myelotec @ London show; Exhibit No. 66.
Marty Wynkoop Aug. 14, 1997 memo to Nick Gounaris re: Myelotec file and device; Exhibit No. 67.
Sep. 9, 1997 unsigned John Moore letter to Jack Snoke; Exhibit No. 68.
Jack Snoke Oct. 6, 1997 letter to James Pastena re: generating revenue and payment of $50k loan; Exhibit No. 69.
Bartolome Gamundi Apr. 7, 1999 status memo to Jim Pastena; Exhibit No. 70.
Michael Mark Sep. 6, 1999 letter to James Pastena; Exhibit No. 71.
James Pastena Sep. 27, 1999 e–mail re; VueCath; Exhibit No. 72.
VueCath Spinal Endoscopy Ssytem, Update Nov. 18, 1998; Exhibit No. 73.
EBI Spine Sales forecast and Historical Data, Mar. 11, 1999; Exhibit No. 74.
Notice of Deposition and Subpoena for Marty Wynkoop in Electro–Biology, Inc., vs. Myelotec, Inc.,Edward J. Lortie, and Adib I. Khoury; Exhibit No. 75.
Felicita Cintron & Jorge A. O'Neill Aug. 20, 1998 Memo to Marty Wynkoop re: VueCath System Manufacturing; Exhibit No. 76.

Marty Wynkoop Mar 8, 1999 e–mail to Evivies with Mar. 12, 1999 handwritten note re: VueCath System Ordering; Exhibit No. 77.

Marty Wynkoop Dec. 3, 1999 Fax to Dr. Mehran Heydarpour with FDA clearance for caudal approach; Exhibit No. 78.

Draft VueCath Spinal Endoscopy System Launch package Jan. 2000; Exhibit No. 79.

Jorge O'Neill Feb. 21, 2000 e–mail to Marty Wynkoop and others re: EPIMED Feb. Order; Exhibit No. 80.

Jorge O'Neill Feb. 23, 2000 & Feb. 25, 2000 e–mail to Marty Wynkoop & others re: EPImed order; Exhibit No. 81.

Jul. 28, 1999 VueCath cost reports; Exhibit No. 82.

Epimed Purchase Orders and Delivery Dates; Exhibit No. 83.

Marty Wynkoop Dec. 18, 1998 Memo to Dave Whyte re: VueCath System Surgery Dec. 10, 1998; Exhibit No. 84.

Charles Muller Feb. 4, 2000 e–mail to Wynkoop and others re; CRI visit Feb. 2, 2000; Exhibit No. 85.

Marty Wynkoop fax to Randy Rizor re: prices; Exhibit No. 86.

Marty Wynkoop Aug. 26, 1998 letter to Randy Rizor re Spinal Accessory Kits; Exhibit No. 87.

Marty Wynkoop Nov. 19, 1998 Wynkoop memo to John Moore re: VueCath Sales Projections; Exhibit No. 88.

Purchase Orders for VueCath; Exhibit No. 89.

Marty Wynkoop Mar. 29, 1999 memo to Dave Whyte re: VueCath spinal Fixation Manufacturing Costs; Exhibit No. 90.

VueCath System EBI Sales Plan; Exhibit No. 91.

John Steen Jan. 29, 1999 letter to John Moore re: pricing for Catheter; Exhibit No. 92.

Marty Wynkoop Jul. 25, 1997 memo to Rich Dickerson, with Rich Dickerson handwritten note to Gounaris re: Myelotec Internet Home Page; Exhibit No. 93.

Jack Snoke Aug. 29, 1997 fax to Marty Wynkoop re: Myelotec activity, particularly in London; Exhibit No. 94.

EBI's response to Respondent Visionary Biomedical,Inc., First Set of Requests for Admission to Petitioner Electro–Biology, Inc., in Electro–Biology, Inc., v. Visionary Biomedical Inc. f/k/a Myelotec, Inc., Edward J. Lortie, and Adib I. Khoury; Exhibit No. 94.

Defendant's Response to Plaintiff's First Request for Production of Documents (from first Arbitration) in Myelotec, Inc., and Edward J. Lortie, Jr., v. Catheter Imaging Systems, Inc.; Exhibit No. 95.

Catheter Imaging Systems, Inc., response to Myelotec, Inc., $1^{st}$ request for Production of Documents (from the $1^{st}$ Arbitration); Exhibit No. 96.

Jun. 19, 1996 Catheter Imaging Systems, Inc., Motion to Dismiss; Exhibit No. 97.

U.S. District Court Northern District of Georgia Atlanta Division in Electro–Biology, Inc., v. Meylotec, Inc., Edward J. Lortie, and Adib I. Khoury, Judge Richard W. Story's Order; Exhibit No. 98.

Declaration of Thomas C. Barthel Jan. 19, 2001 in Electro–Biology, Inc., v. Visionary Biomedical, Inc., (formerly Myelotec, Inc.), Edward J. Lortie, and Adib I. Khoury; Exhibit No. 99.

USPTO list of Thomas C. Barthel Patents; Exhibit No. 100.

Clarus Medical Brochure, Clinical Background, SpineScope Epiduroscope, Clarus Medical, LLC, Minneapolis, MN; Exhibit No. 101.

Gregory Mathison of Clarus Jul. 13, 1992 letter to Office of Device Evaluation, Rockville, Maryland re: Notification for Modification to K912089; Exhibit No. 104.

Gregory Mathison of Clarus Sep. 1, 1992 letter to Office of Device Evaluation, Rockville, Maryland, re: 510(k) Notification for Modification to K912089, Addition of Model 2155 Percutaneous Epidural Spine Scope; Exhibit No. 105.

Gregory Mathison of Clarus Nov. 10, 1992 letter with attachments to Steve Rhodes, Office of Device Evaluation, Rockville, Maryland, re: K925343 Model 2155 Clarus Epidural Spine Scope; Exhibit No. 106.

Miles A. Finn from Clarus Jun. 18, 1993 letter to FDA, Center for Devices and Radiological Health re: K925343 model 2155 Clarus Epidural Spine Scope; Exhibit No. 107.

Jun. 4, 1992 Special Work Order; Cholednchoscope, part No. 500319.001; Exhibit No. 108.

Clarus Interoffice Memo Jun. 9, 1992 from Craig Riedl to Tom Barthel et al., re: Spine Scope, Wrist Scope and Large Joint Scope; Exhibit No. 109.

Jul. 1, 1992 Memo to file from Kate Anderson re: Human Use of spine scope kit. Exhibit No. 110.

Jul. 15, 1992 Memo from Greg Miles to Jim Whit, et al. Re: Discussion with Dr. Stephen Haines regarding spine scope; Exhibit No. 111.

Clarus Interoffice Memo Jul. 8, 1992 from Whit McFarlin to list re: Clinical Game Plan Jul./Aug.; Exhibit No. 112.

Clarus Medical Systems Aug. 27, 1992 memo from Craig Riedl to Miles Finn; re: Trip Report—spine fusion with Dr. Tradnsfeldt; Exhibit No. 113.

Visionary Biomedical, Inc., Activities Calendar; Exhibit No. 114.

Clarus Medical Systems, Inc. Memo Sep. 3, 1992 from Miles to Tom Whit et al. Re: Dr. Transfeldt meeting notes; Exhibit No. 115.

Clarus Medical Systems, Inc., Memo Oct. 26, 1992 to file re: Dr. Transfeldt first cadaver work at Abbott; Exhibit No. 116.

Report on Spine Cadaver Work, Abbott Northwestern Hospital, Oct. 26–29, 1992, Notes by Miles Finn; Exhibit No. 117.

Clarus Medical Systems, Inc., Interoffice Memo Oct. 01, 1992 from Craig Riedl to Miles Finn re: Spine Study Inventory; Exhibit No. 118.

Clarus Medical Systems, Inc., Sep. 16, 1992 letter to Dr. Rune Blomberg, Center Hospital, Norrkoping, Sweden; Exhibit No. 119.

Nov. 27, 1992 Telefax from Rune Blomberg to Miles Finn (Clarus Medical Systems); Exhibit No. 120.

Blomberg Videotape; Exhibit No. 121.

Sep. 7, 1992 Clarus Trip Report from R. Shockey; Exhibit No. 122.

Arbitration Demand Letter Jun. 5, 1996 to Catheter Imaging Systems, Inc.; Exhibit No. 123.

Jul. 12, 1996 Arbitrator Johnson's letter ruling re: Motion to Dismiss in Myelotec, Inc. v. Catheter Imaging Systems, Inc.; Exhibit No. 124.

Dec. 9, 1996 Johnson letter decision in Myelotec, Inc. v. Catheter Imaging Systems,Inc., Exhibit No. 125.

Order and Final Judgment in Catheter Imaging Systems, Inc. v. Myelotec, Inc. and Edward J. Lortie, Jr., dated Feb. 4, 1997; Exhibit No. 126.

EBI's responses to Visionary's claim preclusion summary judgement dated Aug. 21, 2000; Exhibit No. 127.

Declaration of Edwin Bon in Electro–Biology, Inc. v. Myelotec, Inc., Edward J. Lortie, and Adib I. Khoury, dated Jul. 18, 2000; Exhibit No. 128.

EBI Interoffice memo Apr. 7, 1997 from Marty Wynkoop to Rich Dickerson re: Dr. Rizor Visit Apr. 3–4, 1997; Exhibit No. 130.

Michael Mark Apr. 16, 1998 letter to James Pastena; Exhibit No. 131.

May 18, 1999 E–mail from Marty Wynkoop to Rich Dickerson re: New Myleotec Fiberscope; Exhibit No. 132.

Jan. 28, 2000 E–mail from Rich Dickerson to Charles Muller re: VueCath Catheter Marketing; Exhibit No. 133.

May 18, 1999 E–mail from Marty Wynkoop to Marshall Perez re: New Myleotec Fiberscope; Exhibit No. 134.

Jan. 21, 2000 E–Mail from Charles Muller to Marty Wynkoop re: similarities and differences between EBI and Myelotec; Exhibit No. 135.

Jan. 27, 2000 E–Mail from Charles Muller to Marty Wynkoop re: Myelotec Failures; Exhibit No. 136.

EBI Memo Nov. 21, 1997 from Marshall Perez to Rich Dickerson re: VueCath vs. Mylotec Strategy, go out and try to convert the Myelotec customers, Exhibit No. 137.

Nov. 11, 1999 E–Mail from Rich Dickerson to Dr. Racz re: Error in Market Share; Exhibit No. 138.

Mar. 22, 2000 E–Mail from Marshall Perez to Dr Racz re: VueCath Sales; Exhibit No. 139.

3/30/no year, Epimed Meeting minutes; Exhibit No. 140.

Excerpt from EBI 510K submitted Mar. 24, 1997; Exhibit No. 141.

Excerpt from EBI 510K submitted Jul. 16, 1998; Exhibit No. 142.

Declaration of Dr. Luke M. Kitahata in Myelotec, Inc. v. Catheter Imaging Systems, Inc., dated Nov. 18, 1996; Exhibit No. 143.

Excerpts of Videotape deposition of Lloyd Saberski in Myelotec, Inc., and Edward J. Lortie, Jr. v. Catheter Imaging Systems, Inc.; Exhibit No. 144.

Rune G. Blomberg, et al., The Lumbar Epidural Space In Patients Examined with Epiduroscopy The International Anesthesia Research Society 1989 pp. 157–160; Exhibit No. 145.

Rune G. Blomberg, The Lumbar Epidural Space Astra Pain Control, 1991; Exhibit No. 146.

Rune G. Blomberg, The Dorsomedian Connective Tissue Band in the Lumbar Epidural Space of Humans International Anesthesia Research Society 1986, pp. 747–752; Exhibit No. 147.

Rune G. Blomberg, A Method of Epiduroscopy and Spinaloscopy, Acta Anaesthesiol Scand. 1985, pp. 113–116; Exhibit No. 148.

Elias L. Stern, The Spinascope; A New Instrument for Visualizing the Spinal Canal and its Contents Medical Record, pp. 31–32, Jan. 1936; Exhibit No. 149.

J. Lawrence Pool, Myeloscopy; Intraspinal Endoscopy, vol. 11 Surgery, pp. 169–179, Feb. 1942; Exhibit No. 150.

Yoshio Ooi et al.,Myeloscopy, International Orthopaedics 1, pp. 107–111, 1997; Exhibit No. 151.

Bjorn Holmstrom, et al., Epiduroscopic Study of Risk of Catheter Migration Following Dural Puncture By Spinal and Epidural Needles Reg. Anest. 15(1) S:86, 1999; Exhibit No. 152.

James E. Heavner, Percutaneous Evaluation of the Epidural and Subarachnoid Space with a Flexible Fiberscope, Regional Anaesthesia 15 (Supp.);85, 1991; Exhibit No. 153.

Shimoji, et al. Observation of Spinal Canal and Cisternae with the Newly Developed Small–Diameter Flexible Fiberscopes, Regional Anesthesia 15 (Supp.)1988; Exhibit No. 154.

Sven Ivar Seldinger,Catheter Replacement of the Needle In Percutaneou Arteriography vol. 39 Acta Radiologica 368; Exhibit No. 155.

Videotape—Comparing Prior Art Procedures to Procedures Used With Visionary Device; Exhibit No. 168.

Respondent's (Visionary Biomedical, Inc(f/k/a Myelotec, Inc).,Edward J. Lortie, and Adib I. Khoury) Claim Charts Comparing Claims to Prior Art; Exhibit No. 170.

Chart of U.S. Patent 5,342,299, "Steerable Catheter" Serial No. 07/908,403, Filed Jul. 6, 1992, Issued: Aug. 30, 1994; Exhibit No. 171.

Photo Exhibit No. 172.

Appointment and Schedule Calendar for Jul. 8, 1993; Snoke; Exhibit No. 173.

Exhibits 1–4, Exhibit 1, Clarus Manufactured Model 2160 Integral Endoscope/Catheter; Exhibit 2, Visionary Biomedical Manufactured Reproduction of Angiolaz Dual Lumen Steerable Catheter; Exhibit 3, B–Braun Manufactured Dual Lumen Steerable Catheter Model 2000 1995–1999; Exhibit 4, Visionary Biomedical Manufactured Dual– Lumen Steerable Catheter Model 2000 1999–Present; Exhibit No. 175.

American Society Of Regional Anesthesia Syllabus, 24th Annual Meeting and Workshops, "Regional Anesthesia and Pain Medicine" May 6–9, 1999, Philadelphia, Pennsylvania; Exhibit No. 175.

Drawing—Rizor Procedure; Exhibit No. 176.

Drawing—Procedure; Exhibit No. 177.

Patent Database Search Results; "Catheter Imaging Systems" in all years; Exhibit No. 178.

Diagrm of 1995 Agreement; Exhibit No. 179.

Timeline; Exhibit No. 180.

Drawing of Catheter; Exhibit No. 183.

Declaration of Barton W. Bracy in Electro–Biology, Inc. v. Visionary Biomedical, Inc. (formerly Byelotec, Inc.) Edward J. Lortie and Adib I. Khoury dated,Jan. 25, 2001; Exhibit No. 199.

Myelotec, Inc., Financial Statements Jun. 30, 2000 and 1999 (With Independent Auditors' Report Thereon); Exhibit No. 201.

Visionary BioMedical,Inc., Balance Sheet Showing Year to Date Activity as of Period Ending Dec. 31, 2000, for all accounts, Level of Detail; Main sorted by account Number, Exclude Zero Balance Accounts, Exclude closing Entry; Exhibit No. 202.

Visionary BioMedical, Inc., Chart of revenue and Loss for 1994 and 2001; Exhibit No. 203.

Myelotec, Inc., Key Indicator Schedule, Actuals for FY 1997–1998; Exhibit No. 204.

Visionary BioMedical, Inc., Report of Catheter Sales, Jan. 1, 1999–Dec. 31, 2000; Exhibit NO. 205.

Name of Doctors Trained at Myelotec Supported Programs, dated Jan. 12, 2001; Exhibit No. 206.

Declaration of Gerald L. Birchem in Electro–Biology, Inc. v. Visionary Biomedical, Inc,(f/k/a Myelotec, Inc.) Edward J. Lortie, and Adib I. Khoury, dated Jan. 26, 2001; Khoury/Lortie Exhibit No. 1.

Declaration of Adib I. Khoury in Electro–Biology, Inc. v. Visionary Biomedical, Inc,(f/k/a Myelotec, Inc.) Edward J. Lortie, and Adib I. Khoury, dated Jan. 26, 2001; Khoury/Lortie Exhibit No. 2.

Declaration of Edward J. Lortie in Elector–Biology, Inc. v. Visionary Biomedical, Inc, (f/k/a Myelotec, Inc.) Edward J. Lortie and Adib I. Khoury, dated Jan. 26, 2001; Khoury/Lortie Exhibit No. 3.

Certified Copies of Myelotec, Inc. a Domestic Profit Corporation;Certificate of Merger; Certificate of Amendment; Certificate of Restated Articles of Incorporation; Certificate of Incorporation; Khoury/Lortie Exhibit No. 4.

Independent Auditors' Report, Myelotec, Inc., Jun. 30, 1996–Jun. 30, 2000; Khoury/Lortie Exhibit No. 6.

Aug. 22, 1990 FDA letter to Dr. Khoury re; Ultra–Vu Angioscope; Khoury/Lortie Exhibit No. 7.

Dr. Fuad Sabra Apr. 1, 1986 letter to Dr. George Abella re: Recommendation to Dr. Khoury; Khoury/Lortie Exhibit No. 8.

Dr.Sawaya letter (no date) to Dr. George Abella re: Recommendation of Dr Khoury; Khoury/Lortie Exhibit No. 9.

Board Of Medical Examiners Jun. 18, 1997 letter to Dr. Khoury; Khoury/Lortie Exhibit No. 10.

Nov. 15, 1991 Dr. Khoury Letter to Edward Lortie re: AngioLaz undergoing develepment of endoscopic systems under private Label agreement to Solos Endoscopy; Khoury/Lortie Exhibit No. 11.

Rune G. Blomberg, MD and Sven S. Olsson, MD, "The Lumbar Epidural Space in Patients Examined With Epiduroscopy," Anesth. Analg. 1989, 68: 157–160; Khoury/Lortie Exhibit No. 12.

Rune G. Blomberg, MD, "The Lumbar Epidural Space"; Khoury/Lortie Exhibit No. 13.

Rune G. Blomberg, M.D., "The Dorsomedian Connective Tissue Band In the Lumbar Epidural Space of Humans", Anesth. Analg., 1986;65; 747–52; Khoury/Lortie Exhibit No. 14.

Rune G. Blomberg, M.D. "A Method For Epidurasocpy and Spinaloscopy", Anesth. Analg., 1985; 29; 113–116; Khoury/Lortie Exhibit No. 15.

Elias Lincoln Stern, "The Spinascopy: A New Instrument For Visualizing The Spinal Canal And Its Contents", New York, Medical Record, Jan.; Khoury/Lortie Exhibit No. 16.

J. Lawerence Poor, M.D., "Myeloscopy; Intraspinal Endoscopy", Surgery vol. 11, Feb. 1942, No.2; Khoury/Lortie Exhibit No. 17.

Yoshio Ooi et al., "Myeloscopy", International Orthopaedics, pp. 1,107–111, 1997; Khoury/Lortie Exhibit No. 18.

Bjorn Holmstrom, M.D. et al., Epiduroscopic Study of Risk Of Catheter Migration Following Dural Puncture By Spinal And Epidural Needles—A Video Presentation, Department of Anesthesiology, Lindesberg Hospital, Orebro, Sweden; Khoury/Lortie Exhibit No. 19.

James E Heavner DVM et al. "Percutaneous Evaluation Of The Epidural And Subarachnoid Space With A Flexible Fiberscope", Regional Anesthesia 1991; pp. 1551–85; Khoury/Lortie Exhibit No. 20.

Koki Shimoji, M.D., "Observation of Spinal Canal and Cisternae with the Newly Developed Small–Diameter, Flexible Fiberscopes", Anesthesiology 1991; 75: pp. 341–344; Khoury/Lortie Exhibit No. 21.

Sven Ivar Seldinger, "Catheter Replacement of the Needle in Percutaneuos Arteriography", Beontgen Diagnostic Department, Stockholm, Sweden, 1952; Khoury/Lortie Exhibit No. 22.

AngioLaz, "Investigational Device Exemption Application", AngioLaz System II, May 9, 1991; Khoury/Lortie Exhibit No. 23.

MedPRO Month, vol. 1: No. 12, Dec., 1991; Khoury/Lortie Exhibit No. 25.

Brouchure, Dynapace Systems, Inc, Introduces The New Epidural Ultra VU Scope System, ASA Meeting–San Francisco, CA, Oct. 28–30, 1991; Khoury/Lortie Exhibit No. 26.

Dr. Khoury May 6, 1996 letter to Dr. Randy Rizor, re: Epidural Scope; Khoury/Lortie Exhibit No. 27.

Yale Videos; RX–36, 37, 38; Khoury/Lortie Exhibit No. 28.

Photos of Epidural Scope; Khoury/Lortie Exhibit No. 29.

Angiolaz Incorporated, Rockingham, VT., Drawing No. AS–509;Khoury/Lortie Exhibit No. 30.

"Interventional Intraspinal Techniques Using A Visually Guided Epidural Catheter", Dr. Randy Rizor et al., Case Reports; Khoury/Lortie Exhibit No. 32.

Dr. Randy Rizor Jun. 8, 1992 letter to Dr. David Brandenburg, Institutional Review Committee re: Presenting the procedure of epiduroscopy to the Review Committee; Khoury/Lortie Exhibit No. 33.

Edward Lortie Oct. 15, 1992 letter to Dr. Khoury re: Offer of position of Vice–President of Busness Development; Khoury/Lortie Exhibit No. 34.

Catheter Imaging Systems Board of Directors Meeting Notes Jul. 20, 1993; Khoury/Lortie Exhibit No. 35.

Handwritten notes from Jul. 20, 1993 Catheter Imaging Systems Board of Directors Meeting; Khoury/Lortie Exhibit No. 36.

Myelotec, Inc., Stock Subscription Agreement, dated Oct. 25, 1993; Khoury/Lortie Exhibit No. 38.

Michael G. Cassaro—Southeast Seminars, Inc., May 27, 1994 letter to Dr. Khoury re; Misrepresentation in a course manual; Khoury/Lortie Exhibit No. 39.

Settement Agreement between Catheter Imaging Systems, Inc., P. Jack Snonke, Michael J. Mark, William J. Mack, Myelotec, Inc., and Edward J. Lortie, dated May, 1995; Khoury/Lortie Exhibit No. 42.

Dismissal With Prejudice in Catheter Imaging Systmes, Inc. v. Edward J. Lortie, Michael Mark, William J. Mack and P. Jack Snoke, dated Jun. 16, 1995; Khoury/Lortie Exhibit No. 43.

James C. Grant Nov. 21, 1995 letter to Edward J. Lortie and William R. Johnson re: Notice of Dispute; Khoury/Lortie Exhibit No. 44.

William H. Needle May 24, 1996 letter to Catheter Imaging Systems, Snoke, Mark, Mack, James C. Grant, Esq., re: Notice of Dispute, Claim of Patent Invalidity; Khoury/Lortie Exhibit No. 45.

Sumner Rosenberg Jun. 5, 1996 letter to James D. Johnson, Esq., Catheter Imaging Systems, Inc., P. Jack Snoke, re: Notice of Arbitration Demand, Claim of Patent Invalidity; Khoury/Lortie Exhibit No. 46.

James C. Grant Jun. 19, 1996 letter to James D. Johnson, Edward Lortie and Myelotec, Inc., Re: Jun. 5, 1996 Arbitration Demand; Khoury/Lortie Exhibit No. 47.

James D. Johnson Jul. 12, 1996 letter to Sumner Rosenberg, Esq., James C. Grant, Esq., Re: Arbitration between Myelotec, Inc. (Myelotec) v. Catheter Imaging Systems, Inc. (CIS); Khoury/Lortie Exhibit No. 48.

James D. Johnson Dec. 9, 1996 letter to Sumner Rosenberg, Esq., Jeffrey S. Whittle, Esq., Re: Myelotec, Inc. v. Catheter Imaging Systems, Inc.,Khoury/Lortie Exhibit No. 49.

Myelotec Memo to Edward Lortie from Dr. Khoury, dated Feb. 24, 1997 Re: Dr. Khoury's resignation; Khoury/Lortie Exhibit No. 50.

James Pastena, EBI Medical Systems, Apr. 20, 1999 letter to Edward J. Lortie, Re: issued patents; Khoury/Lortie Exhibit No. 51.

Declaration in Support of Petition For Correction of Inventorship Under 37 C.F.R. §1.48 (a) in application of Phillip J. Snoke et al., Serial No. 07/908,403, Filed Jul. 6, 1992, For Steerable Catheter, datedJul. 24, 1992; Khoury/Lortie Exhibit No. 52.

Declaration in Support of Petition for Correction Of Inventorship Under 37 C.F.R. §1.48 (a) in application of Phillip J. Snoke, et al., Serial No. 07/970,490, Filed: Nov. 2, 1992, For: Catheter Having Multiple Durometer; Khoury/Lortie Exhibit No. 53.

Edward J. Lortie Apr. 21, 1999 letter to James Patesna, President EBI Medical Systems, Inc.; Khoury/Lortie Exhibit No. 54.

James Pastena Apr. 30, 1999 letter to Edward Lortie Re: letter dated Apr. 21, 1999; Khoury/Lortie Exhibit No. 56.

James Pastena May 28, 1999 letter to Edward Lortie in response to May 6, 1999 letter with executed Confidentiality Agreement; Khoury/Lortie Exhibit No. 56.

Edward J. Lortie Jun. 3, 1999 letter to James Pastena, Re: Confidentiality Agreement; Khoury/Lortie Exhibit No. 57.

James Pastena Jun. 25, 1999 letter to Edward J. Lortie, Re: Patent Application for: Steerable Catheter Having Segmented Tip And One–Piece, Inlet Housing, And Method Of Fabricating Same; Khoury/Lortie Exhibit No. 58.

AnioLaz Epiduroscope Apr. 6, 1992, List of examined patients and prognosis; Khoury/Lortie Exhibit No. 59.

Catheter Imaging Systems, Inc., Jul. 9, 1993 Minutes of Meeting; Khoury/Lortie Exhibit No. 60.

Edward J. Lortie May 11, 1994 letter to Mr. Jamie Grooms, University of Florida—Tissue Bank, Re: G&G Marketing Plan; Khoury/Lortie Exhibit No. 61.

Jerry Birchem Dec. 1, 1999 letter to Pete Dambach, EBI Medical Systems, Re: Financial and general information on the Myelotec Spine business; Khoury/Lortie Exhibit No. 62.

Complaint in Electro–Biology, Inc. v. Myelotec, Inc., Edward J. Lortie and Adib I. Khoury, dated Oct. 27, 1999; Khoury/lortie Exhibit No. 63.

Ricard D. Harris May 15, 2000 letter to James D. Johnson, Esq., Re: Electro–Biology, Inc. v. Myelotec, Inc., et al., Re: Settlement Agreement dated 5/95; Khoury/Lortie Exhibit No. 64.

Video Tape—"Exploring Epidural Endoscopy," Madison Avenue, RX 15 Copy.

Video Tape—"Epidural Endoscopy/Exercise and Comments," Yale University School of Medicine Center for Pain Management, RX 26, Copy.

Video Tape—Angio Laz, Tapes S1, S2, S3, RX 36; MYE 14657, Duplicate Copy.

Video Tape—Angio Laz, Tapes S4, S5,S6, RX 37; MYE 14659, Duplicate Copy.

Video Tape—Angio Laz, Tapes S7, S8, S9, RX 38; MYE 14659, Duplicate Copy.

Video Tape—"Discussion with Dr. Saberski," Apr. 6, 1992; RX 25, Copy.

Video Tape—Presentation 3/ Presentation 2; MYE 015464, Myelotec, Respondents Ex. 168. Copy.

Video Tape—Deposition of Dr. Lloyd Saberski Nov. 7, 1996 (RT 1:44)—Edited Version, Copy.

Petitioner Response in Electro–Biology, Inc. v. Myelotec, Inc., Edward J. Lortie and Adib I. Khoury, dated Sep. 2, 2000; Exhibit No. 92.

Defendants reply and Certificate of Service in Electro–Biology, Inc. v. Myleotec, Inc., Edward J. Lortie,and Adib I. Khoury, Dated Aug. 23, 2000,Exhibit 90.

Correspondence from Bradley K. Groff to James D. Johnson re: Withdrawing as Arbitrator in Electro–Biology, Inc. v Myelotect et al., Dated Aug. 18, 2000;Exhibit 87.

Correspondence, dated May 19, 2000, from John S. Paccocha to James D. Johnson in Electro–Biology, Inc. v. Myelotect, Inc., et al., with copy of "Petitioners Response to Respondents Myelotec's Motion for EBI to Designate a Limited Set of Claims On Which to Proceed," Exhibit No. 83.

Motion filed along with Certificate of Service in Electro–Biology, Inc. v. Myelotec, Inc., Edward J. Lortie, and Adib I. Khoury, Dated Jul. 26, 2000; Exhibit 79.

May 22, 2000 Correspondence from Bradley K. Groff to James D. Johnson re: Arbitration: Electro–Biology, Inc. v. Myelotec, Inc., et al.;Myelotec, Inc., response; Exhibit No. 30.

May 22, 2000 Correspondence from Bradley K. Groff to James D. Johnson re: Arbitration: Electro–Biology, Inc. v Myelotec, Inc., et al.; Response from Edward J. Lortie; Exhibit No. 29.

May 22, 2000 Correspondence from Bradley K. Groff to James D. Johnson re: Arbitration: Electro–Biology, Inc. v. Myelotec, Inc., et al.; Response from Adib I. Khoury; Exhibit No. 28.

May 15, 2000 Correspondence from Richard D. Harris to James D. Johnson re: Electro–Biology, Inc. v. Myelotec, Inc., et al.; re: Settlement Agreement dated May, 1995; Exhibit No. 26.

May 15, 2000 Correspondence from James H. Patterson to Richard D. Harris, Bradley K. Groff and Mitchell G. Stockwell, re: Pending Issues in Electro–Biology, Inc. v. Visionary BioMedical, et al.; Exhibit No. 184.

Apr. 3, 2001 Correspondence from James Patterson to Richard D. Harris, Bradley K. Groff, Joseph Bankoff, Mitchell B. Stockwell, re: Motions for reconsideration from Petitioner and Respondents in Electro–Biology, Inc. v. Visionary BioMedical, et al.; Exhibit No. 182.

Petitioners Motion for Reconsideration of the Arbitrator's Memorandum and Final Order in Electro–Biology, Inc. v. Visionary Biomedical, Inc., dated Mar. 28, 2001; Exhibit No. 181.

Defendants Motion and Supporting Brief Seeking Supplementation and Reconsideration of Certain Portions of the Arbitrator's Order in Electro–Biology, Inc. v. Visionary Biomedical, Inc., dated Mar. 27, 2001; Exhibit No. 179.

Visionary Biomedical, Inc.'s Proposed Findings of Facts in Electro–Biology, Inc. v. Visionary Biomedical, Inc., dated Feb. 19, 2001; Exhibit No. 171.

Petitioner Electro–Biology Inc.'s Proposed Findings of Fact in Electro–Biology, Inc. v. Visionary Biomedical, Inc., dated Feb. 19, 2001; Exhibit No. 170.

Feb. 19, 2001 Correspondence from Matthew D. Josephic to James Patterson Re: copies of Respondent Edward J. Lortie's Proposed Findings of Fact and Respondent Adib I. Khoury's Proposed Findings of Fact in Electro–Biology, Inc. v. Visionary Biomedical, Inc.; Exhibit No. 168.

Respondents's Claim Charts and Memoranda Submitted Pursuant to Arbitrator's Oct. 31, 2000 Order with Certificate of Service in Electro–Biology, Inc. v. Visionary Biomedical, Inc., dated Dec. 5, 2000; Exhibit No. 143.

Dec. 5, 2000 Correspondence from John S. Pacocha to James H. Patterson in Electro–Biology, Inc. v. Visionary BioMedical, Inc., Re; Notifying of forwarding Petitioner EBI's Final Claim Construction Memoranda and Claim Charts by email and FedEx.; Exhibit No. 142.

Nov. 17, 2000 Correspondence from Kristin Mallatt to Richard D. Harris in Electro–Biology, Inc. v. Visionary BioMedical, Inc., Re: Interrogatories; Exhibit No. 139.

Respondents' Claim Charts with Certificate of Service in Electro–Biology, Inc. v. Visionary Biomedical, Inc., Dated Nov. 14, 2000; Exhibit No. 137.

Nov. 14, 2000 Correspondence from Richard D. Harris to James H. Patterson in Electro–Biology, Inc. v. Visionary BioMedical, Inc., Re; Sending of Petitioner EBI's Claim Charts by email and copy by FedEx.; Exhibit No. 136.

pp. 836–838, 1040–1042 and 1060–1062 from the transcript of the hearing held in 2001 before Abritrator Patterson.

* cited by examiner

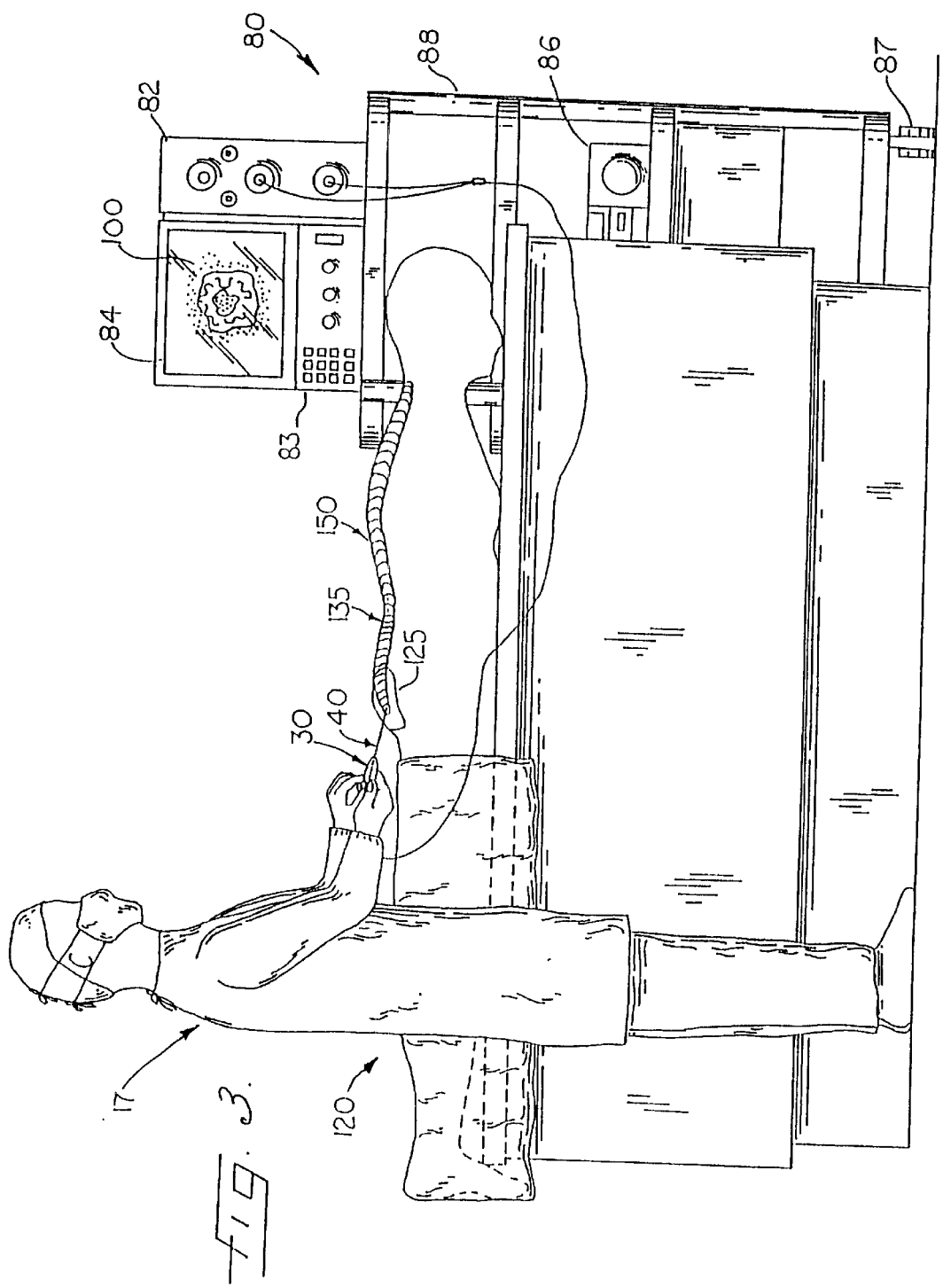

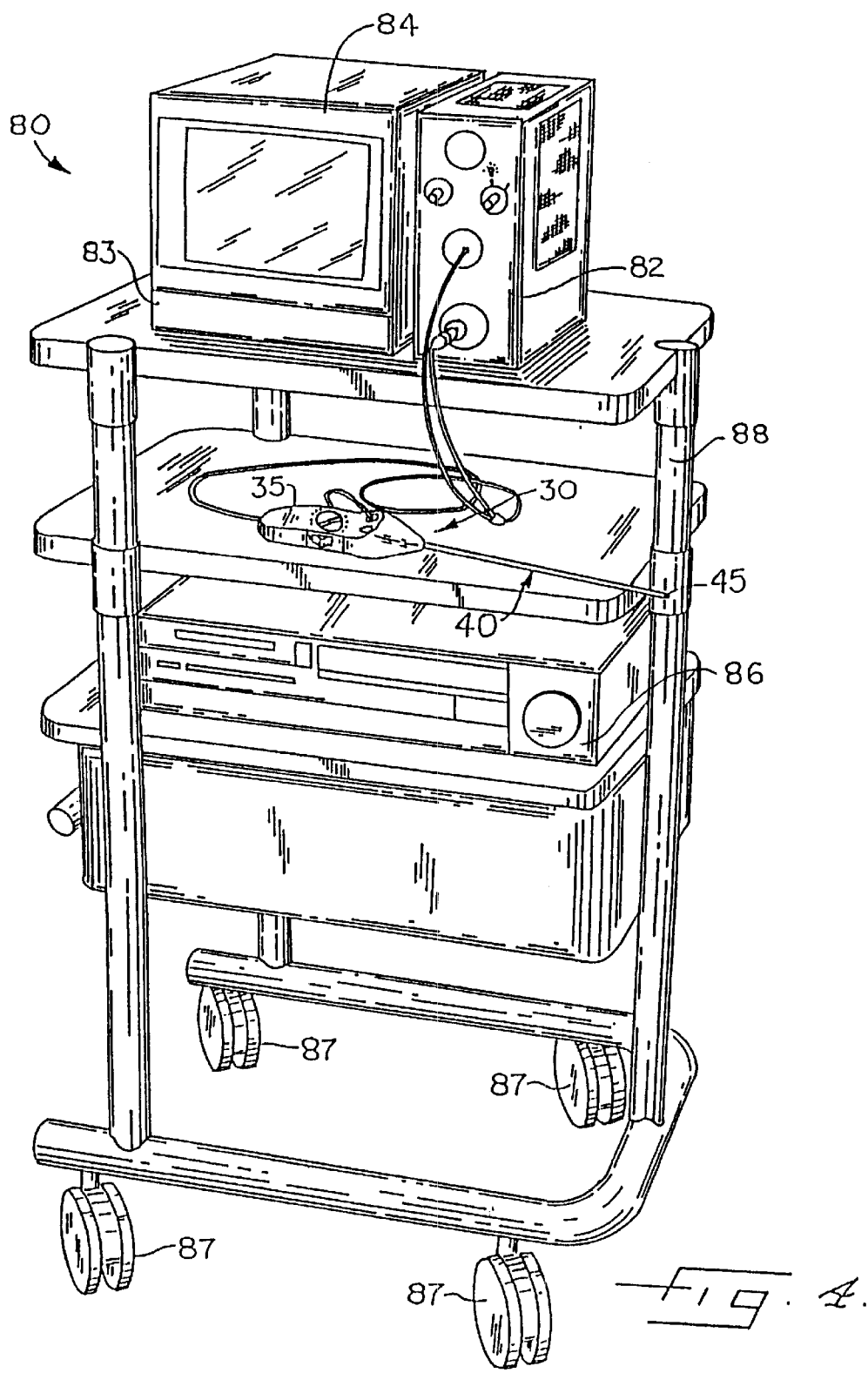

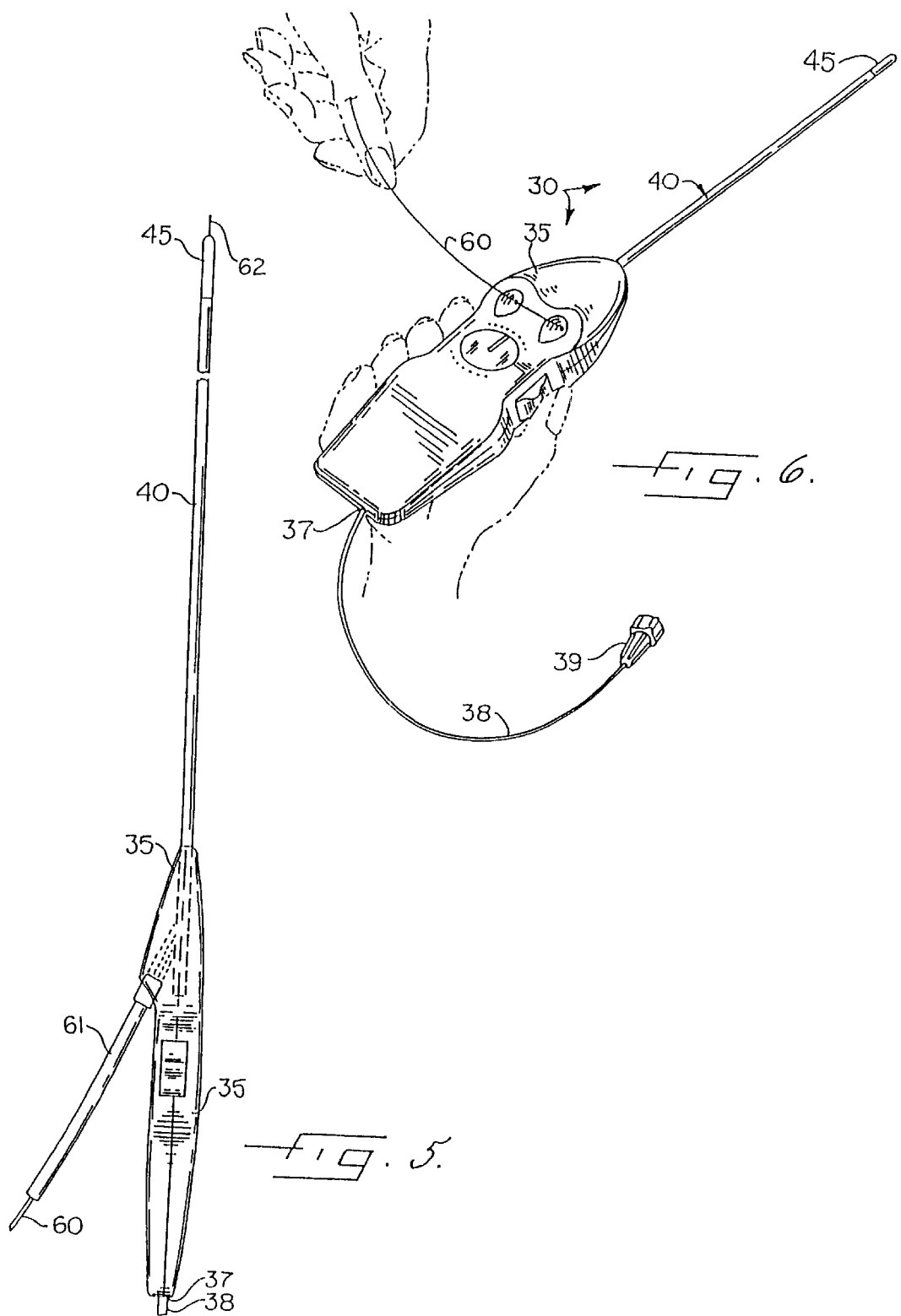

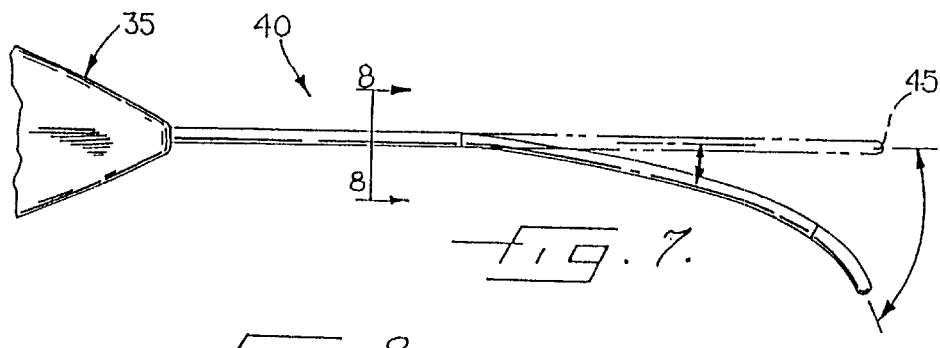
Fig. 7.
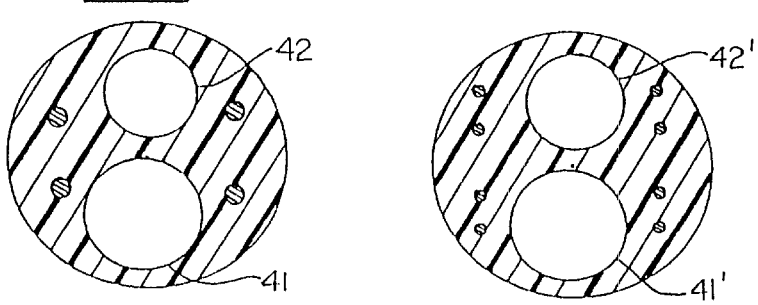
Fig. 8.
Fig. 9.
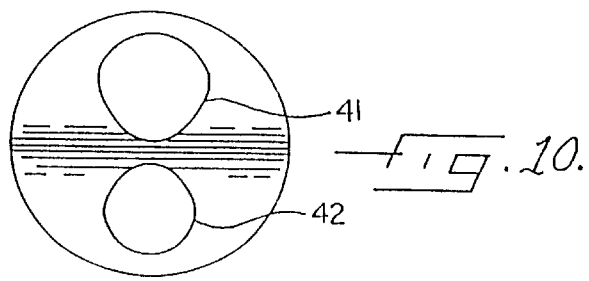
Fig. 10.
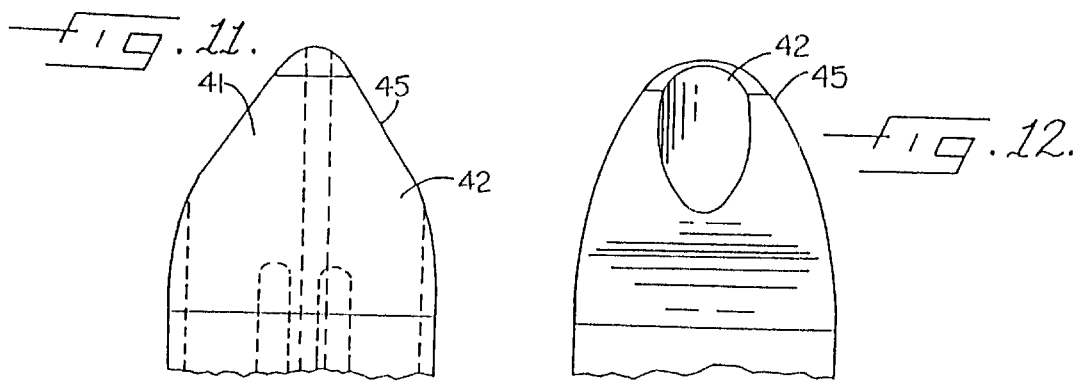
Fig. 11.
Fig. 12.

METHOD OF EPIDURAL SURGERY

RELATED APPLICATIONS

This application is a continuation of Ser. No. 09/066,884 filed on Apr. 27, 1998 now U.S. Pat. No. 6,010,493, which is a continuation of U.S. Ser. No. 08/957,998, filed Oct. 22, 1997, now U.S. Pat. No. 5,857,996, which is a continuation of U.S. Ser. No. 08/606,084 filed Feb. 23, 1996, now ABN, which is a continuation of U.S. Ser. No. 08/321,174 filed Oct. 11, 1994, now U.S. Pat. No. 5,496,269, which is a continuation of U.S. Ser. No. 08/129,331, filed Sep. 30, 1993, now U.S. Pat. No. 5,354,266 which is a continuation-in-part of U.S. Ser. No. 07/908,403, filed Jul. 6, 1992, now U.S. Pat. No. 5,342,299, which is a continuation-in-part of U.S. Ser. No. 07/963,431 filed Oct. 19, 1992, now U.S. Pat. No. 5,423,311, which is a continuation-in-part of U.S. Ser. No. 07/970,490 filed Nov. 2, 1992 now U.S. Pat. No. 5,399,164.

FIELD OF THE INVENTION

This invention relates to surgical methods, and more particularly to methods of epidural surgery in and around the epidural space.

BACKGROUND OF THE INVENTION

Back pain, and particularly lower back pain, is a major expense to society and is one of the most common disabling problems of those of working age. Injuries to the back vary from herniated disks of the spine to muscle strains and nerve damage. In the back or posterior end of the human body, the epidural space is potential space located in and extending the length of the spine. The epidural space is defined along one edge or side by the dura mater which surrounds the spinal cord. The epidural space is further defined along a second edge or side by the periosteum of the bony vertebrae or by the ligamentum-flavum at the vertebral interspaces. Along the interior surface of the ligamentum-flavum lies the venus plexus, a complex configuration of veins. The epidural space contains fat, connective tissue, blood vessels, lymphatic vessels, nerve fibers, and other structures. Various lesions, cystical masses, and nerve damage can occur in and around the epidural space which causes various back problems for the human body.

Although applying anesthesia to the epidural space has been known for procedures such as child birth or the like, the anatomy of the epidural space and related structures has not been fully investigated. Conventionally, the insertion of a catheter, fluid introducer, or the like for inducing spinal anesthesia directly into the subarachnoid space of the spinal column, such as seen in U.S. Pat. No. 5,232,442 by Johnson, et al. entitled "Method And Apparatus For Inducing Anesthesia", has been through fluoroscopic or radiographic observation. Fluoroscopic observation techniques have also been used to try to locate the various sources of problems associated with back pain such as seen in U.S. Pat. No. 5,215,105 by Kizelshteyn, et al. entitled "Method Of Treating Epidural Lesions". The fluoroscopic techniques are helpful for general guidance of instruments or other devices, but fail to give the physician or other medical personnel a detailed picture of structures within vessels or cavities, such as the epidural space, and therefore are limited in identifying the source of back pain problems.

Also, endoscopes have been used whereby internal areas or organs within a body vessel or cavity may be observed by inserting an elongated insertable part of the endoscope through a tube or sleeve inserted into a body vessel or cavity, or directly into the body vessel or cavity itself, such as seen in U.S. Pat. No. 5,195,541 by Obenchain entitled "Method Of Performing Laparoscopic Lumbar Discectomy". An endoscope, as used herein, is an instrument for examining the interior of a bodily canal or hollow organ. A catheter, on the other hand, is a tube inserted into a bodily channel, such as a vein, to maintain an opening to a body vessel or cavity. These endoscopes, however, are relatively large with respect to a catheter and, therefore, do not cooperate with a catheter for performing delicate surgery such as the type surrounding the back or spinal column.

Further, fiber optic scopes or fiberscopes have been used for various types of surgery such as surrounding the heart. These fiberscopes often are inserted into a vein or an artery for viewing blockage or the like within the vein or artery. The epidural space, however, has not fully been explored using visual techniques because the epidural space, as described above, does not take the form of a vein or artery. Because the epidural space collapses around an instrument or device inserted therein such as a catheter, an endoscope, a fiberscope, or a cutting tool, the space has not been considered for optical scope viewing or for performing many types of epidural surgical procedures.

Therefore, there is still a need for a method of epidural surgery that allows a physician to effectively enter the epidural space of a patient, visually observe and document a problem area which could be the source of back pain in the patient, and therapeutically treat the problem area in or around the epidural space in a minimal amount of time and with minimal amount of cutting and other potential damage to the patient during surgery.

SUMMARY OF THE INVENTION

The present invention provides a method of epidural surgery that improves visibility in the epidural space of a patient for more effectively conducting therapeutic surgery therein. The method of epidural surgery involves distending a portion of the epidural space by filling the portion of the epidural space with a fluid supplied from a catheter positioned in the epidural space and positioning a portion of an optical scope in the distended portion of the epidural space by inserting the optical scope through the catheter to thereby provide a visual image of the epidural space. The method of epidural surgery also allows a physician, or other medical personnel, to control and manipulate the catheter and an imaging source while simultaneously using surgical tools, such as fiberoptic scopes or the like, and fluids needed for medical operations to thereby allow the physician to positionally locate, isolate, and view problem areas within the epidural space. Because the method of epidural surgery minimizes cutting and other potential damage to the patient during surgery, the invention provides a method of epidural surgery that often can be performed as an outpatient procedure.

BRIEF DESCRIPTION OF THE DRAWINGS

Some of the objects and advantages of the present invention having been stated, others will become apparent as the description proceeds when taken in conjunction with the accompanying drawings, in which:

FIG. 3 is an elevational plan view of a surgical operation on a patient having a catheter positioned through an opening in the sacrum region and into the epidural space by a physician for therapeutic treatment of a problem area according to a first embodiment of the present invention;

FIG. 4 is perspective view of an imaging apparatus for the methods according to the present invention;

FIG. 5 is a side elevational view of a catheter having a fiberscope inserted therein for the methods according to the present invention;

FIG. 6 is a perspective view of a catheter having a fiberscope inserted therein for the methods according to the present invention;

FIG. 7 is fragmentary top elevational view of a catheter for the methods according to the present invention;

FIG. 8 is an enlarged cross-sectional view of a first embodiment of a catheter taken along line 8—8 of FIG. 7 for the methods according to the present invention;

FIG. 9 is an enlarged cross-sectional view of a second embodiment of a catheter taken along line 8—8 of FIG. 7 for the methods according to the present invention;

FIG. 10 is an enlarged distal end plan view of a catheter taken from a distal end thereof for the methods according to the present invention;

FIG. 11 is enlarged fragmentary top plan view of a distal end of a catheter and having phantom lines therein illustrating the positioning of the multiple lumens within the catheter for the methods according to the present invention;

FIG. 12 is enlarged fragmentary side plan view of a distal end of a catheter for the methods according to the present invention;

DESCRIPTION OF ILLUSTRATED EMBODIMENTS

The present invention now will be described more fully hereinafter with reference to the accompanying drawings in which a preferred embodiment of the invention is shown. Like numbers refer to like elements throughout.

Figure 1:
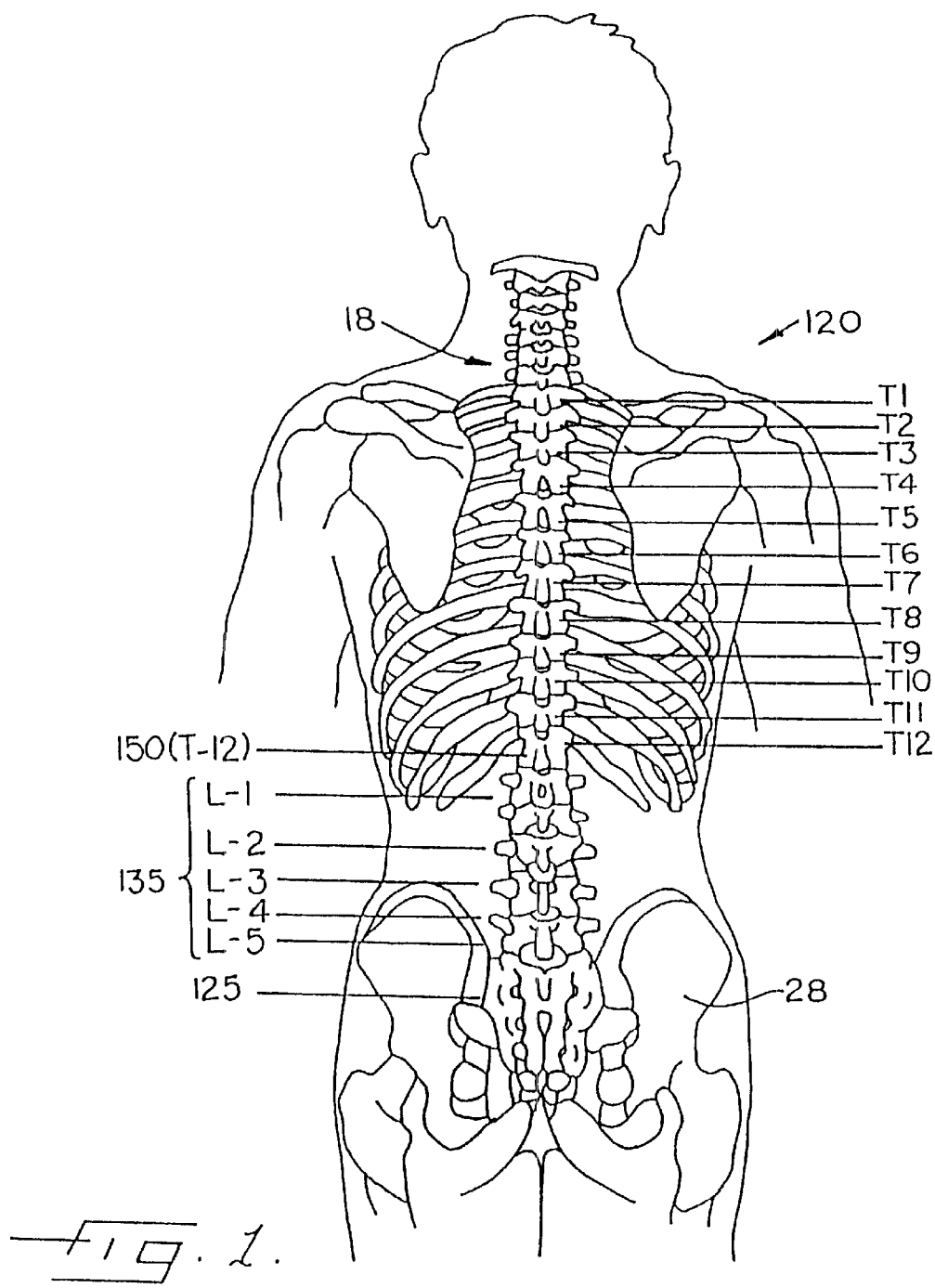
FIG. 1 is a fragmentary skeletal view of a human body illustrating spinal column regions thereof.
Figure 2:
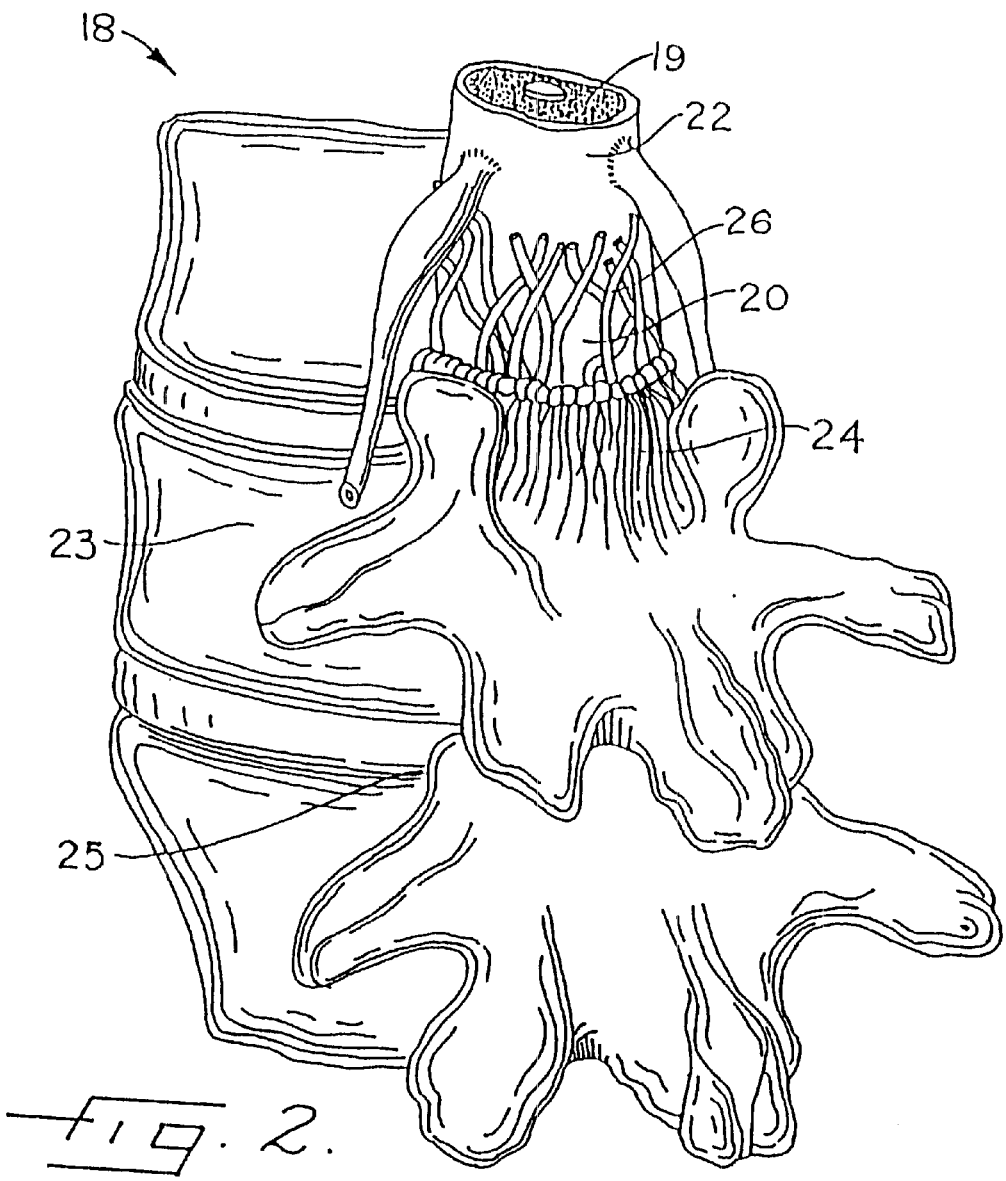
FIG. 2 is a fragmentary view of a spinal column illustrating the position of the epidural space therein.

In the back region or posterior end of the human body, as best illustrated in FIGS. 1 and 2, the epidural space 20 is potential space located in and extending the length of the spine 18. As illustrated in the fragmentary view of a spinal region 18 in FIG. 2, the epidural space 20 has a generally cylindrical or crescent type shape and is defined along one edge or side by the dura mater 22 which surrounds the spinal cord 19. The epidural space is further defined along a second edge or side by the periosteum of the bony vertebrae 23 or by the ligamentum-flavum 24 at the vertebral interspaces 25. Along the interior surface of the ligamentum-flavum 24 lies the venus plexus 26, a complex configuration of veins. The epidural space 20 is a collapsible potential space that contains fat, connective tissue, blood vessels, lymphatic vessels, nerve fibers, and other structures. Various lesions, cystical masses, and nerve damage can occur in and around the epidural space which causes various back problems for the human body. For example, fibrosis ranging from soft to tougher scar tissue may form randomly or in layers and adhere to the dura mater 22 and the periosteum of the body vertebrae 20 or the. ligamentum-flavum 24 which form lesions extending across the epidural space 20. These lesions can be caused by post operative scarring of nerves such as from laminectomy procedures. A ruptured, leaking, or torn disk can also cause lesions which are often the source of back pain.

The method of epidural surgery according to the present invention improves visibility in the epidural space 20, of a patient for more effectively conducting therapeutic surgery in and around the epidural space 20 such as applying a steroic fluid, performing a diskectomy, or disrupting a fibrotic lesion. The method of epidural surgery according to the present invention involves distending a portion of the epidural space 20 by filling the portion of the epidural space 20 with a fluid, preferably a liquid such as a normal saline solution, supplied from a catheter 30 positioned in the epidural space 20. As best shown in FIGS. 3–6, a portion of an optical scope 60 is positioned in the distended portion of the epidural space 20 by inserting the optical scope 60 through the catheter 30 to thereby provide a visual image 100 of the epidural space 20.

According to first and second embodiments of the present invention, the catheter 30 may be one of the numerous types of catheters known to those skilled in the art, but preferably is a multi-lumen, steerable catheter 30 as best illustrated with reference to FIGS. 5–12. The multi-lumen, steerable catheter 30 preferably has a multiple durometer tube portion 40 extending outwardly from a handle portion 35 such as disclosed and described in copending U.S. patent applications Ser. No. 07/908,403 filed on Jul. 6, 1992 and Ser. No. 07/970,490 filed on Nov. 2, 1992 which are hereby incorporated herein by reference. The optical scope 60 is preferably an 0.88 millimeter (mm) fiberscope, known to those skilled in the art, that may be inserted through a lumen 42 of the steerable catheter 30, and preferably through a fiberoptic sheath 6 as shown in FIG. 5 and have a portion 62 thereof extend into the epidural space 20. The fiberscope 60 preferably communicates with an imaging apparatus such as disclosed and described in copending U.S. patent application Ser. No. 07/963,431 filed on Oct. 12, 1992 which is also hereby incorporated herein by reference. As such, further details of the steerable catheter 30, the optical scope 60, and the imaging apparatus 80 will not be discussed except in relation to the operation thereof for the methods of epidural surgery according to the present invention.

By providing the combination of the steerable catheter 30, the fiberscope 60, and the imaging apparatus 80, as illustrated in the elevational plan view of FIG. 3, a physician 17, or other medical personnel, can control and manipulate the catheter 30 and the imaging source 82 of the imaging apparatus 80 while simultaneously using surgical tools, such as cutting instruments or the like, and fluids needed for medical operations to thereby allow the physician to positionally locate, isolate, and view problem areas on a television monitor 84, i.e., cathode ray tube display device, within the epidural space 20. The imaging apparatus 80 enables the physician to not only observe the visual image 100 of the distended portion of the epidural space 20, but also provides a means for recording and documenting the problem area such as the video cassette recording 86 mounted below the imaging source 82 and television monitor 84 on the portable stand 88. Since the steerable catheter 30 is preferably quite flexible and maneuverable within the epidural space 20, as best shown in FIGS. 6 and 7, the method also provides less radical interspinal surgical operations because problem areas can more effectively be observed and accessed with the optical scope 60 and steerable catheter 30 combination. Because the imaging apparatus 80 is mounted on a stand 88 having wheels 87, as best shown in FIGS. 5, the physician 17, and other medical personnel, can position the apparatus 80 close to the operation site. The control panel 83 and imaging source 82 of the imaging apparatus 80 provides image 100 adjustments, focus, and magnification to assist in viewing the epidural space 20 and the problem area when the portion of the epidural space 20 is distended by the liquid. It will be understood that the distended portion of the epidural space 20 to be viewed is preferably an amount of the epidural space 20 less than the entire boundaries thereof, the boundaries or peripheries being previously defined and described with reference to FIG. 3.

Figure 13:
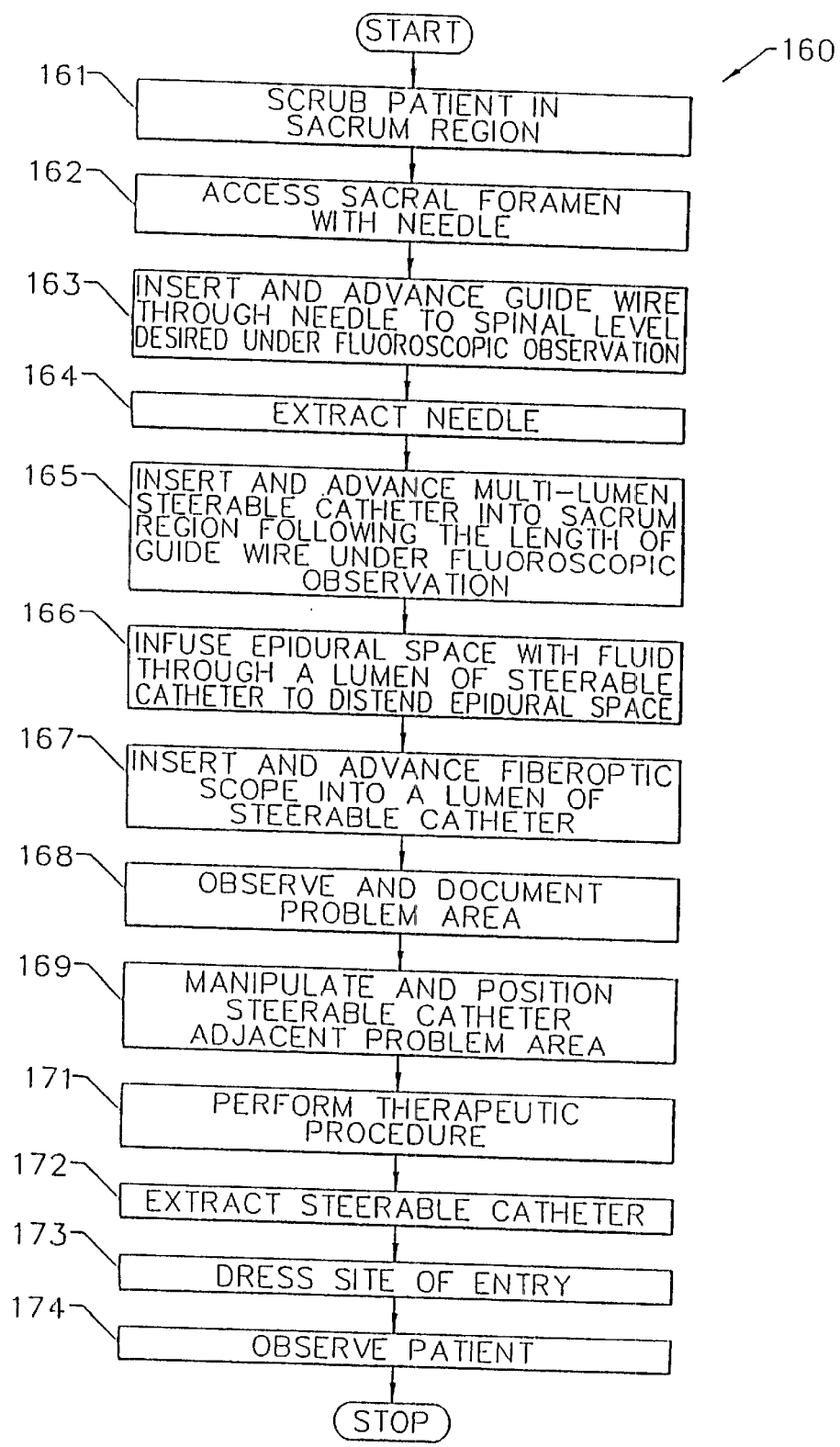
FIG. 13 is a block diagram of a method of epidural surgery according to a first embodiment of the present invention.
Figure 14:
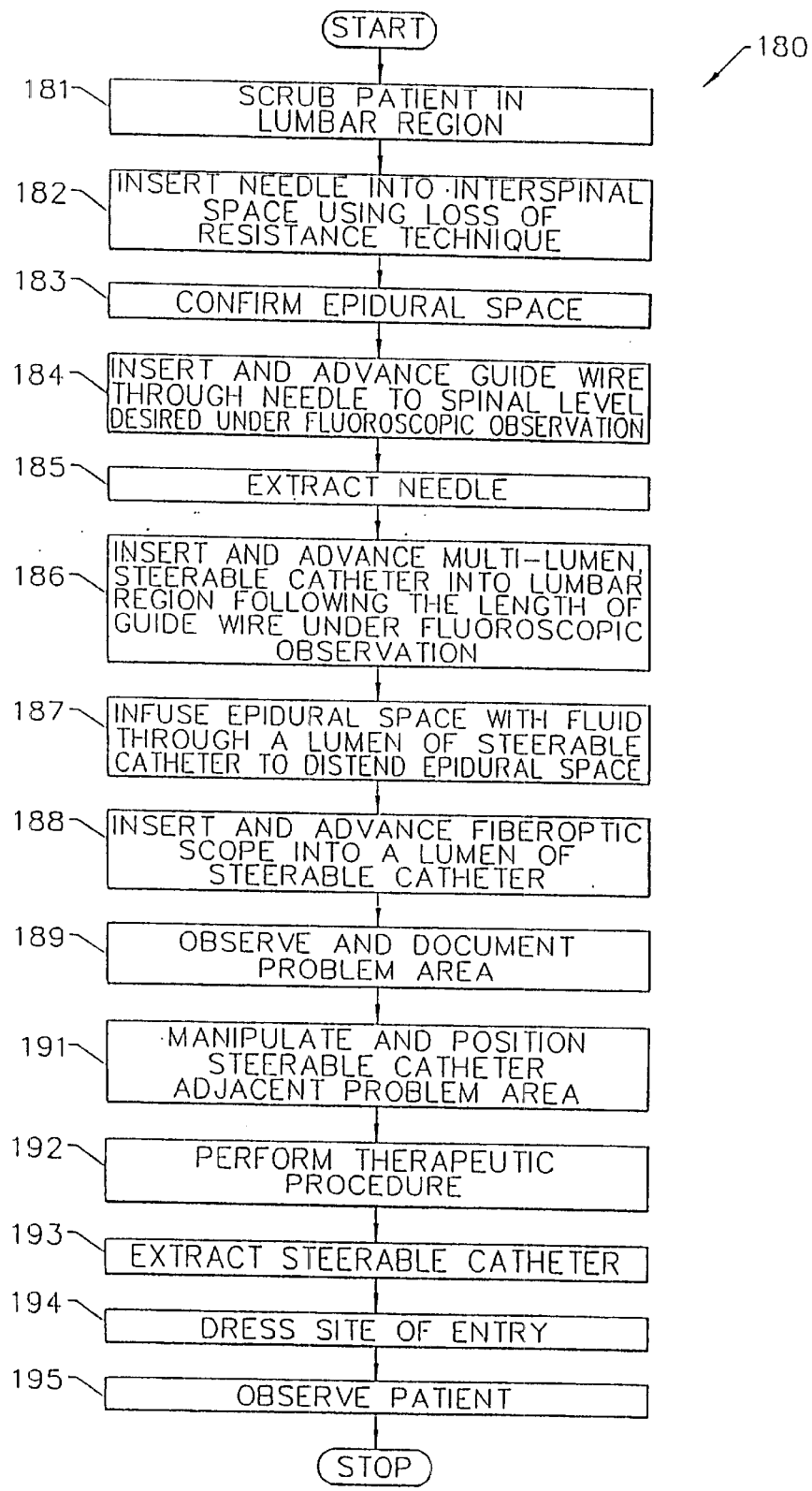
FIG. 14 is a block diagram of a method of epidural surgery according to a second embodiment of the present invention.

More particularly with reference to the block diagrams illustrated in FIGS. 13 and 14, and the elevational plan view of a surgical operation in FIG. 3, the method of epidural surgery according to the present invention includes inserting a needle through the skin of a patient 120, preferably through a sacrum region 125 (FIG. 13) or a lumbar region 135 (FIG. 14) of the patient 120, and into the epidural space 20 to thereby provide an opening from the skin into the epidural space 20 of the patient 120.

As illustrated in FIG. 1, the sacrum region 125 is at a lower end of the spinal column 18 below L-5 and adjacent the pelvic region 28. The sacrum 125 is a triangular shape bone formed generally by five fused vertebrae, i.e., sacral vertebrae, that are wedged dorsally between the two hip bones of the pelvic region 28 in this region of the human anatomy. It will also be understood by those skilled in the art that the invention is also applicable to various animals for veterinarian epidural procedures. The lumbar region 135 extends from L-1 to L-5 between the sacrum region 125 at a lower end and the thorax region (T-1 to T-12) at an upper end. The thorax region (T-1 to T-12) from an upper part 150 (T-12) lumbar region 135 to neck.

As illustrated in FIG. 13, according to a first embodiment of a method of epidural surgery 160 according to the present invention, the patient is scrubbed in the sacrum region 125, preferably in an area around the sacral canal and up to the level of T-8 (FIG. 1) with wide prep iodine, as shown by block 161. The patient 120 is draped, the physician 17 is scrubbed, and dressed in a sterile gown (FIG. 3). The entry site is prepared and a one percent (1%) Xylocaine solution is injected to create a skin wheel. The patient 120 is then sedated with Versed which is individually titrated to the patient's needs. The patient is also monitored with pulse oximetry, EKG, and a blood pressure monitor 42.

After the patient is scrubbed and prepared, a needle, preferably an 18-gauge Touhy needle, is used to access the sacral foramen, as shown by block 162. The ligamentum-flavum 24 (FIG. 2) is pierced and the needle tip is inserted in the sacral hiatus. Under fluoroscopic guidance, as shown by block 163, a guide wire, preferably a 0.035-inch straight tip floppy guide wire, is inserted and advanced through the needle and into the epidural space. The guide wire is preferably radiopaque and formed of stainless steel with a Teflon coating. The physician 17 then preferably fluoroscopically observes the position of the guide wire in the epidural space 20 and advances the guide wire to a spinal level where a suspected problem area within the epidural space 20 may have originated. As shown by block 164, the needle is extracted from the epidural space 20 and preferably discarded.

The catheter 30, and preferably a multi-lumen, steerable catheter, is then inserted over the guide wire and into the opening to the epidural space 20, as shown by block 165. The guide wire functions as a guidance device as the catheter 30 is advanced into the sacral hiatus; Because the catheter 30 is preferably a steerable catheter, the handle 35 and flexible distal end 45 ease the advancement and positioning of the catheter 30 within and around the epidural space 20. Fluid is supplied, and preferably continuously supplied, to a lumen 42 of the steerable catheter 30 to thereby distend a portion of the epidural space 20. The fluid is preferably a liquid such as a normal saline solution. A normal saline bag can be accessed with an I.V. set and coupled to a three-way stopcock, or valve for fluid regulation. A 20 cubic centimeter (cc) syringe is then coupled-to a second port of the three-way stop-cock. An access port to a lumen 42 of the catheter 30 is also preferably coupled to a third port of the stop-cock. The,fluid may also enter through tube portion 38 at a proximal end 37 at the handle portion 35 of the catheter 30 (as best shown in FIG. 6). The 20 cc syringe is used first to extract all the air bubbles from the I.V. set and then fill the I.V. set with a normal-saline, liquid solution for distention of the epidural space. Twenty cc's of saline can be infused into the epidural space 20, as shown by block 166. The 20 cc's are sufficient to increase the pressure in a portion of the epidural space 20 and create a cavity in which the nerve root or other structures can be observed. The position of the steerable-catheter 30 within. the epidural space may also be fluoroscopically observed. The catheter 30, like the guide wire, is also preferably radiopaque. Under such circumstances, the physician can advance the steerable catheter 30 under the fluoroscopical observation to the suspected problem area.

As shown by block 167, an optical scope 60, preferably a fiber optic scope or fiberscope, is then inserted preferably within another lumen 41 of the multi-lumen, steerable catheter 30. The fiberscope 60 can enter an access port in the handle portion 35, as best shown in FIG. 6, or enter at a proximal end 37 of the handle portion 35 as shown in FIG. 3 or 4. It will also. be understood that the fiberscope 60 can be inserted prior to the advancement of the catheter 30 in the epidural space 20. A portion of the optical scope 60 is advanced within the lumen 41 of the steerable catheter 30 and into the distended portion of the epidural space 20. The optical scope 60 preferably is not radiopaque and preferably will not extend into the epidural space 20 more than about one centimeter (cm). With the fluid distending a portion of the epidural space 20, the optical scope 60 can also be positioned within the distal tip 45 of catheter 30 and still view the distended portion of the epidural space 20. The optical scope 60 illuminates the distended portion of the epidural space 20 to thereby visualize and display the epidural space 20 and a problem area therein with the imaging apparatus 80, as shown by block 168. The catheter 30 can be manipulated to place the distal end 45 into an optimal position to avoid any adhesions or naturally occurring fat globules that could hinder the flow of drugs such as a steroic fluid or that could hinder positioning of instruments or devices used in surgical procedures. As shown by block 169, the catheter 30 is manipulated until the problem area such as an inflammation is recognized by its redness, increased vascularity, or other systems. The problem area is then observed and documented. As shown by block 171, a treatment is then performed to the problem area within the epidural space such as the applying of a steroic fluid to a nerve area, disrupting a fibrotic lesion, performing a diskectomy, or other types of procedures. These therapeutic treatments preferably include positioning a distal end 45 of the steerable catheter 30 adjacent the problem area within the epidural space 20 and treating the problem area within the epidural space 20 through a lumen 41 or 42 of the steerable catheter 30.

After performing the treatment, the catheter 30 is then slowly extracted and a dressing is placed at the site of entry, as shown by blocks 172, 173. The patient is observed, preferably for about two hours, then discharged, as shown by block 174. The patient's chart is completed and a one week follow-up appointment may be made.

As illustrated in FIG. 14, according to a second embodiment 180 of a method of epidural surgery of the present invention, a lumbar region 135 of the patient 120 is scrubbed and prepped, preferably in and around the L3–L4 area (FIG. 1), as shown by block 181. In this second embodiment, in contrast to the first embodiment as illustrated in FIG. 2, the patient 120 is preferably in a sitting position to spread the L1–L5 vertebrae to make access easier. It will also be understood that other sites of entry along the spinal column 18, besides the sacrum or caudal region 125 and lumbar region 135 of the patient 120, may be performed according to the present invention.

As shown by block 182, an 18-gauge Touhy needle is inserted into the interspinal space,. such as between L3 and L4, using the loss of resistance technique well known to those skilled in the art. The epidural space 20 is confirmed and a guide wire, preferably a 0.035-inch straight floppy top guide wire, is inserted and advanced through the needle to the spinal level where the suspected problem area may be located in and around the epidural space 20, as shown by blocks 185, 186. The needle is then extracted (block 185) and preferably discarded.

As shown by block 187, the catheter 30 is inserted and advanced over the guide wire to the suspected problem area. The epidural space 20 is then infused with a fluid, as previously described with reference to the first embodiment, and distended (block 187). A portion of the optical scope 60 is inserted and advanced through a lumen 41 of the catheter 30 and 10 into the distended portion of the epidural space 20, as shown by block 188. The problem area is observed and documented, and the catheter is manipulated and positioned adjacent the problem area for more effectively performing a therapeutic procedure, such as previously described (blocks 189, 191). A therapeutic procedure is then performed, also as previously described, as shown by block 192. The catheter 30 is then slowly extracted, the entry site is dressed, and the patient is observed (blocks 193–195). A follow-up visit is then scheduled and the patient discharged.

The method of the present invention thereby provides improved visualization of the epidural space and more effective treatment of problems areas therein.

The method allows the physician to effectively observe and document the problem area and then determine the most effective treatment for the patient. Since the steerable catheter is preferably quite flexible and maneuverable within the epidural space, the method also provides less radical interspinal surgical operations because problem areas can more effectively be observed and accessed with the optical scope and steerable catheter combination.

In the drawings and specification, there have been disclosed typical preferred embodiments of the invention and, although specific terms are employed, they are used in a generic and descriptive sense only and not for the purposes of limitation. The invention has been described in considerable detail with specific reference to various embodiments. It will be apparent, however, that various modifications and changes can be made within the spirit and scope of the invention as described in the foregoing specification and defined in the following appended claims.

That which is claimed is:

1. A method of enhancing viewing within the epidural space of a patient during an epidural procedure, the method comprising:

inserting a distal end portion of a steerable catheter through an opening in a patient and into the epidural space, the steerable catheter having a plurality of lumen formed in an elongate tube portion having a tube diameter, said plurality of lumen including at least a first working lumen and a second working lumen, each of said first and second working lumen having distinct, non-coincident longitudinal axes, each of said first and second working lumen being separated from each other by a portion of the elongate tube, with each of said first and second working lumen being substantially symmetrically positioned along both sides of said tube diameter, a handle connected to the elongate tube portion, at least one access port connected to the handle and in fluid communication with the elongate tube portion to provide access to the plurality of lumen, and a steering controller connected to the handle and associated with the elongate tube to steeringly control movement of at least the distal end of the elongate tube portion;

passing a fluid through said first working lumen of the steerable catheter;

distending a portion of the epidural space of the patient by filling the portion of the epidural space with the fluid supplied from the steerable catheter to thereby create a fluid cavity within the epidural space;

inserting a fiber optic scope through the second working lumen of the same steerable catheter when the distal end portion of the same steerable catheter is positioned in the epidural space;

viewing the fluid cavity by use of the inserted fiber optic scope; and steering the steerable catheter to a structure within the epidural space for further viewing.

2. A method as defined in claim 1, wherein the step of inserting a fiber optic scope includes the step of connecting the fiber optic scope to an imaging apparatus which displays the visual image received from the fiber optic scope.

3. A method as defined in claim 1, wherein the step of distending a portion of the epidural space includes the step of supplying fluid to the steerable catheter and to the epidural space from the steerable catheter to the extent to maintain the portion of the epidural space in an open position for adequately visualizing the epidural space.

4. A method as defined in claim 1, wherein the step of inserting a fiber optic scope includes the step of advancing the fiber optic scope through the second working lumen of the steerable catheter and into the epidural space.

5. A method as defined in claim 1, wherein the step of passing a fluid through the first working lumen includes continuously supplying fluid through the first working lumen to the epidural space.

6. A method as defined in claim 5, wherein the step of steering includes advancing the distal end portion of the tube portion to a suspected problem area, and wherein the method further comprises treating the suspected problem area through at least one of the plurality of lumen of the steerable catheter.

7. A method as defined in claim 1, wherein said elongate tube portion is substantially circular in shape, said first working lumen having a first cross-sectional diameter, said second working lumen having a second cross-sectional diameter, the first and second cross-sectional diameters being substantially coincident with the tube diameter of said substantially circular elongate tube portion.

8. A method as defined in claim 7, wherein the first and second cross-sectional diameters are substantially unequal in size.

9. A method as defined in claim 1, wherein distending the portion of the epidural space comprises delivering the fluid supplied from the steerable catheter into the epidural space in a direction substantially parallel with a line of sight extending from the fiber optic scope to a portion of the fluid cavity viewed by the fiber optic scope, the line of sight being defined as an imaginary line from the fiber optic scope to the portion of the fluid cavity viewed by the fiber optic scope.

10. A method as defined in claim 1, wherein distending the portion of the epidural space comprises directing the delivery of fluid supplied from the steerable catheter into the epidural space so as to create sufficient fluid pressure against the preselected portion of tissue to thereby create a fluid cavity.

11. A method as defined in claim 1, wherein distending the portion of the epidural space comprises connecting a syringe containing the fluid to said first working lumen, injecting fluid from the syringe into said first working lumen, and conveying the fluid through said first working lumen into the portion of the epidural space.

12. A method as defined in claim 1, wherein distending the portion of the epidural space comprises positioning a fluid container in fluid communication with said first working lumen, delivering fluid from the container into the first working lumen and conveying the fluid through the first working lumen into the portion of the epidural space.

13. A method as defined in claim 12, wherein distending the portion of the epidural space further comprises regulating fluid pressure within the fluid cavity by interposing a stop-cock in fluid communication with and between the container and said first working lumen to thereby control the amount of fluid supplied to the fluid cavity and the rate at which the fluid is supplied.

14. A method as defined in claim 1, wherein distending the portion of the epidural space comprises directing the delivery of fluid supplied from the steerable catheter into the epidural space to a preselected portion of tissue within the epidural space so as to create sufficient fluid pressure against the portion of tissue to thereby create and maintain a fluid cavity.

15. A method as defined in claim 1, wherein continuously supplying a fluid through the first working lumen of said steerable catheter, and into the epidural space, comprises providing a stop-cock having at least three access ports defining first, second, and third access ports respectively, connecting the steerable catheter to the first access port, connecting a syringe containing fluid to the second access port, and connecting a fluid container to the third access port.

16. A method as defined in claim 15, wherein continuously supplying a fluid through the steerable catheter and into the epidural space comprises opening the first and second access ports to permit injection of the fluid from the syringe into the steerable catheter and through the steerable catheter into the epidural space to thereby distend the portion of the epidural space, closing the second access port and opening the third access port to permit fluid to flow from the container into the steerable catheter and through the steerable catheter in to the epidural space to thereby maintain the portion of the epidural space in a distended state.

17. A method as defined in claim 15, wherein the injection of the fluid from the syringe into the steerable catheter and through the steerable catheter into the epidural space comprises injecting fluid from a syringe capable of delivering at least twenty cubic centimeters (20 cc) of fluid into the steerable catheter and through the steerable catheter into the epidural space.

18. A method as in claim 15, wherein the flow of fluid from the container into the steerable catheter and through the steerable catheter into the epidural space comprises permitting fluid to flow into the steerable catheter from a pliable intravenous (I.V.) bag.

19. A method as defined in claim 18, wherein continuously supplying fluid through the steerable catheter and into the epidural space comprises controlling the amount of fluid supplied into the epidural space and the rate at which fluid is supplied into the epidural space from the I.V. bag using the third access port of the stop-cock.

* * * * *